(12) United States Patent
Guedat et al.

(10) Patent No.: US 10,675,257 B2
(45) Date of Patent: Jun. 9, 2020

(54) METHOD OF TREATING CANCER WITH A COMBINATION OF BENZYLIDENEGUANIDINE DERIVATIVES AND CHEMOTHERAPEUTIC AGENT

(71) Applicant: InFlectis BioScience, Nantes (FR)

(72) Inventors: Philippe Guedat, Montenois (FR); Pierre Miniou, Nantes (FR)

(73) Assignee: INFLECTIS BIOSCIENCE, Nantes (FR)

( * ) Notice: Subject to any disclaimer, the term of this patent is extended or adjusted under 35 U.S.C. 154(b) by 0 days.

(21) Appl. No.: 15/749,485

(22) PCT Filed: Jul. 26, 2016

(86) PCT No.: PCT/EP2016/067791
§ 371 (c)(1),
(2) Date: Jan. 31, 2018

(87) PCT Pub. No.: WO2017/021216
PCT Pub. Date: Feb. 9, 2017

(65) Prior Publication Data
US 2018/0221310 A1   Aug. 9, 2018

(30) Foreign Application Priority Data
Jul. 31, 2015   (EP) .................................. 15306256

(51) Int. Cl.
*A61K 31/44*   (2006.01)
*A61K 31/155*   (2006.01)
(Continued)

(52) U.S. Cl.
CPC ........ *A61K 31/155* (2013.01); *A61K 31/4188* (2013.01); *A61K 31/44* (2013.01); *A61K 31/519* (2013.01); *A61P 35/00* (2018.01)

(58) Field of Classification Search
CPC .............................. A61K 31/155; A61K 31/44
(Continued)

(56) References Cited

FOREIGN PATENT DOCUMENTS

| WO | WO 2013/049045 A1 | 4/2013 | |
|---|---|---|---|
| WO | WO-2013049045 A1 * | 4/2013 | ........... A61K 31/433 |

(Continued)

OTHER PUBLICATIONS

Anderson, Chem & Biology (2003), vol. 10, pp. 787-797. (Year: 2003).*

(Continued)

*Primary Examiner* — Craig D Ricci
*Assistant Examiner* — Janet L. Coppins
(74) *Attorney, Agent, or Firm* — Knobbe, Martens, Olson & Bear, LLP

(57) ABSTRACT

The present invention relates to a composition for use in treating a glioma or ameliorating the effects of a glioma, particularly glioblastoma, wherein said composition comprises a first active agent selected from the group consisting of a compound of formula (I), or a pharmaceutically acceptable salt thereof, (I) and a second active agent, which is temozolomide, or a pharmaceutically acceptable salt thereof; and a pharmaceutically acceptable carrier.

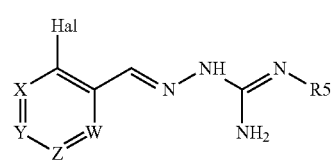

(I)

13 Claims, 3 Drawing Sheets

(51) Int. Cl.
    *A61K 31/519*     (2006.01)
    *A61P 35/00*     (2006.01)
    *A61K 31/4188*     (2006.01)

(58) Field of Classification Search
    USPC ........................................................ 514/357
    See application file for complete search history.

(56) References Cited

FOREIGN PATENT DOCUMENTS

| WO | WO 2014/108520 A1 | 7/2014 | |
| WO | WO-2014108520 A1 * | 7/2014 | ........... A61K 31/155 |

OTHER PUBLICATIONS

Thiel, Nature Biotechnology (2004), vol. 22(5), pp. 513-519. (Year: 2004).*

* cited by examiner

METHOD OF TREATING CANCER WITH A COMBINATION OF BENZYLIDENEGUANIDINE DERIVATIVES AND CHEMOTHERAPEUTIC AGENT

TECHNICAL FIELD

The present invention relates to the use of a combination of benzylideneguanidine derivatives and temozolomide in the manufacture of a medicament for use in the treatment of cancer. In particular the cancer to be treated is a brain tumour, more particularly a glioma, more particularly still a glioblastoma multiforme (GBM) and the preferred combination comprises guanabenz and temozolomide.

BACKGROUND OF THE INVENTION

Brain and central nervous system (CNS) tumors are a diverse group of cancers that arise in the brain, meninges, spinal cord, and other parts of the CNS. They may be classified as benign or malignant, and may be primary in origin or metastatic.

Gliomas are one of the most frequent types of nervous system tumors. Gliomas comprise nearly half of all primary brain tumours and a fifth of all primary spinal cord tumours. Gliomas are tumours of the glial cells most often astrocytes; these cells support and protect nerve cells in the brain. Gliomas may occur anywhere in the brain or spinal cord, including the cerebellum, brain stem, or optic chiasm. Gliomas often carry a poor prognosis and thus are among the most devastating diseases. Of all brain tumors diagnosed each year, about half are malignant gliomas and result in death within 18 months.

Gliomas can be divided into two groups based on their growth characteristics: low-grade gliomas and high-grade gliomas. Low-grade gliomas are usually localized and grow slowly over a long period of time. Examples of low-grade gliomas include astrocytomas, oligodendrogliomas, pilocytic astrocytomas. Over time, most of these low-grade gliomas dedifferentiate into more malignant high-grade gliomas that grow rapidly and can easily spread through the brain. Examples of high-grade gliomas include anaplastic astrocytoma and glioblastoma multiforme.

Glioblastoma multiforme (GBM), also known as spongioblastoma multiforme, is the most common of these, accounting for 45.2% of all malignant brain and CNS cancers (Ostrom et al., 2014 The epidemiology of glioma in adults: a "state of the science" review. Neuro-Oncology, 16(4), 896-913). The annual incidence of GBM varies from 5 to 7 per 100,000: each year, about 25,000 new cases are diagnosed in the European Union and about the same number in the United States. Signs and symptoms depend on several factors (size, rate of growth, localization of the tumor) and are mainly represented by headaches, seizures, neurological deficits, and changes in mental status.

The treatment for gliomas generally involves surgical removal, followed by a course of radiation and chemotherapy. As for current chemotherapy, temozolomide, an oral methylating chemotherapeutic agent, became the standard of care for newly diagnosed GBM, when used concurrently with external beam radiation followed by adjuvant therapy. In patients with newly diagnosed GBM, current standard treatments provide median overall survival of a little over one year. In patients with relapsed or progressive GBM, the prognosis is particularly poor. Almost all patients with GBM die within five years.

Temozolomide (TMZ) (brand names Temodar and Temodal and Temcad) also known as 3,4-dihydro-3-methyl-4-oxoimidazo [5,1-d]-as-tetazine-8-carboxamide (see U.S. Pat. No. 5,260,291), is an oral chemotherapy drug used in glioma therapy, with little to no success. It is an alkylating agent used for the treatment of GBM—as well as for treating melanoma, a form of skin cancer. Temozolomide is also indicated for relapsed Grade III anaplastic astrocytoma. Temozolomide is a prodrug and an imidazotetrazine derivative of the alkylating agent dacarbazine. The therapeutic benefit of temozolomide depends on its ability to alkylate/methylate DNA, which most often occurs at the N-7 or 0-6 positions of guanine residues. This methylation damages the DNA and triggers the death of tumor cells. However, some tumor cells are able to repair this type of DNA damage, and therefore diminish the therapeutic efficacy of temozolomide, by expressing a protein O6-alkylguanine DNA alkyltransferase (AGT) encoded in humans by the O-6-methylguanine-DNA methyltransferase (MGMT) gene. In some tumors, epigenetic silencing of the MGMT gene prevents the synthesis of this enzyme, and as a consequence such tumors are more sensitive to killing by temozolomide. Conversely, the presence of AGT protein in brain tumors predicts poor response to temozolomide and these patients receive little benefit from chemotherapy with temozolomide.

Even with the combination of radiotherapy plus temozolomide, median survival was 14.6 months at a median follow-up of 28 months (Stupp et al., New England J. Med., 352:987 (2005)). The two-year survival rate was 26.5 percent with radiotherapy plus temozolomide and 10.4 percent with radiotherapy alone.

Therefore, in spite of the introduction of temozolomide, further research for the development of new agents active against glioma is warranted in order to prevent drug resistance. Indeed, there is still an unmet medical need for new potent agents for the treatment of gliomas. The present invention is directed to meeting this and other needs.

The present inventors have discovered that the compound 2-(2,6-dichlorobenzylidene)hydrazinecarboximidamide, also referred to as guanabenz, and various guanabenz derivatives disclosed herein, when used in combination with conventional chemotherapeutic agents, such as temozolomide, provide synergistic anti-tumor responses in an in vivo model of glioma compared to conventional chemotherapeutic agents such as temozolomide when used alone.

Guanabenz:

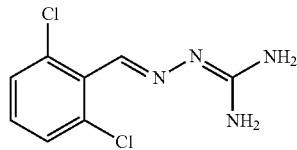

is an alpha agonist of the alpha-2 type that was used as an antihypertensive drug. In addition, guanabenz and some guanabenz derivatives protect cells from otherwise lethal accumulation of misfolded proteins in the endoplasmic reticulum (ER), a phenomenon called ER stress which activates the Unfolded Protein Response (UPR) which meticulously coordinate adaptive and apoptotic responses to ER stress. Guanabenz and some guanabenz derivatives are acting by binding to a regulatory subunit of protein phosphatase 1, PPP1R15A (GADD34), selectively disrupting the stress-induced dephosphorylation of the α subunit of translation initiation factor 2 (eIF2α). Thus, guanabenz and some guanabenz derivatives set the translation rates in stressed cells to a level manageable by available chaperones, thereby restoring protein homeostasis. It was reported that guanabenz does not bind to the constitutive PPP1R15B (CReP) and therefore does not inhibit translation in non-stressed cells (Tsaytler et al., 2011 Science 332 pp 91-94; Das et al., 2015 Science 348 pp 239-242).

ER stress is present in cancer cells; indeed following initiation of malignancy, rapid tumour growth and inadequate vascularization result in micro-environmental stress which activates the UPR. Enhanced ER stress signalling and increased chaperone expression is linked to drug resistance and constitutes an adaptive capacity of cancer cells to maintain ER protein homeostasis (or proteostasis), thereby counteracting apoptosis (Yadav et al. 2014 J. Cancer Prevention 19 pp 75-88; Lee et al. 2008 Neuro-oncology 10 pp 236-243). The UPR, when coupled with induced tumour dormancy, dually protects neoplastic cells from apoptosis and permits recurrence once favourable growth conditions have been restored. However, if ER stress is prolonged and the UPR fails to restore ER proteostasis, tumour cell apoptosis ensues (Vandewynckel et al. 2013 Anticancer Res. 33 pp 4683-4694).

Thus, cancer treatments with chemotherapeutic agent and PPP1R15A inhibitors to restore protein homeostasis have been proposed:

EP2059233 discloses the use of PPP1R15A inhibitor in combination with a second product used in cancer treatment, such as etoposide or mitomycin C, to prepare a pharmaceutical composition to prevent or treat cancer in mammals.

WO2010/054381 discloses the use of non-selective PPP1R15A inhibitor, salubrinal, in combination with a proteasome inhibitor such as bortezomib to prepare a pharmaceutical composition to prevent or treat cancer in mammals;

WO 2008/061647 (Acure Pharma AB) discloses the use of N-(2-chloro-3,4-dimethoxybenzylideneamino)guanidine as a VEGFR inhibitor and its associated applications in the treatment or prevention of undesired blood vessel formation during tumour growth.

US2014/0235556 discloses methods and combination of temozolomide and various marketed drugs to treat gliomas. Moreover, US2014/0235556 shows that the combination of temozolomide and intraperitoneally administered guanabenz has no anti-tumor effect in a rodent model of gliomas.

Unexpectedly, the present inventors have now discovered that guanabenz and various guanabenz derivatives disclosed herein, when used in combination temozolomide, provide synergistic anti-tumor responses in an in vivo model of glioma. These findings offer a new approach to the treatment of cancer, particularly gliomas, and more particularly glioblastomas.

SUMMARY OF THE INVENTION

The present invention provides combinations, compositions and methods useful for treating a cell proliferative disorder.

According to a first object, the present invention concerns a combination of:
a first active agent selected from the group consisting of compound of formula (I), or a pharmaceutically acceptable salt thereof,

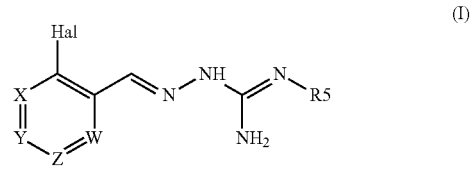

wherein:
Hal=Cl, F, Br or I
W is either CR4 or —N=;
X is either CR1 or —N=;
Y is either CR2 or —N=;
Z is either CR3 or —N=;
R1 is selected from H, Hal, alkyl, O-alkyl;
R2 is selected from H, Hal, alkyl, O-alkyl and C(O)R6;
R3 is selected from H, Hal, alkyl, O-alkyl;
R4 is selected from is H, Cl, F, Br or I;
R5 is selected from O—R7 or H, alkyl, cycloalkyl, aralkyl, alkenyl, cycloalkenyl, heterocyclyl, aryl, C(O)-alkyl and C(O)-aryl, each of which is optionally substituted with one or more R8 groups;
R6 is selected from OH, =O, CN, COO-alkyl, aralkyl, heterocyclyl, SO2-alkyl, Salkyl, SO-alkyl, SO2-aryl, COOH, CO-alkyl, CO-aryl, NH2, NH-alkyl, N(alkyl)2, CF3, alkyl and alkoxy;
R7 is H or alkyl, cycloalkyl, aralkyl, alkenyl, cycloalkenyl, heterocyclyl, aryl, C(O)-alkyl, and C(O)-aryl, each of which is optionally substituted with one or more R8 groups;
R8 is selected from the group consisting in H, OH, =O, CN, COO-alkyl, aralkyl, heterocyclyl, SO2-alkyl, Salkyl, SO-alkyl, SO2-aryl, COOH, CO-alkyl, CO-aryl, NH2, NH-alkyl, N(alkyl)2, CF3, alkyl and alkoxy;
Or a prodrug, tautomer, or a pharmaceutically acceptable salt thereof,
Where said first active agent is in an oral, intravenous, epidural, intracerebral or intracerebroventricular route, preferably an oral or intravenous dosage form.
and
a second active agent, which is temozolomide, a prodrug thereof, or a pharmaceutically acceptable salt thereof, where the first and second active agents are for simultaneous, separate or sequential use.

It is to be understood that the first and second active agents may be formulated either in the same composition or in separate composition, either within the same or distinct packagings.

Further, they may be in the same or distinct dosage forms.

Accordingly, kits comprising the first and second active agents in separate forms and/or compositions are encompassed by the invention.

According to an embodiment, the first and second active agents may be formulated in the same or different formulations.

According to an embodiment, the first active agent is in an oral dosage form.

According to an embodiment, the second active agent is in an oral or intravenous oral dosage form.

According to an embodiment, the first and second active agents are in oral dosage forms, in the same or separate compositions, of the same or different formulations.

According to an embodiment, the first and second active agents are in the same oral dosage form, within a single formulation.

According to a further object, the present invention concerns the combination as defined above for use for the treatment and/or prevention of proliferative disorders, such as a glioma, wherein said compound of formula (I) is administered via the oral, intravenous, epidural, intracerebral or intracerebroventricular route.

In another object, the present invention also concerns the combination of the invention as defined above for use in preventing or treating a glioma or ameliorating the effects of a glioma.

According to an embodiment, the glioma is a glioblastoma, in particular a glioblastoma multiforme.

According to another object, the present invention also concerns the method for treating or preventing glioma or ameliorating the effects of a glioma, particularly glioblastoma multiforme, comprising administering to a patient in need thereof a combination of the invention as defined above.

According to a further object, the present invention also concerns a pharmaceutical composition comprising
a first active agent selected from the group consisting of compound of formula (I), or a pharmaceutically acceptable salt thereof,

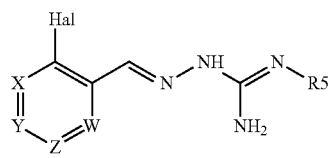

(I)

wherein:
Hal=Cl, F, Br or I
W is either CR4 or —N=;
X is either CR1 or —N=;
Y is either CR2 or —N=;
Z is either CR3 or —N=;
R1 is selected from H, Hal, alkyl, O-alkyl;
R2 is selected from H, Hal, alkyl, O-alkyl and C(O)R6;
R3 is selected from H, Hal, alkyl, O-alkyl;
R4 is selected from is H, Cl, F, Br or I;
R5 is selected from O—R7 or H, alkyl, cycloalkyl, aralkyl, alkenyl, cycloalkenyl, heterocyclyl, aryl, C(O)-alkyl and C(O)-aryl, each of which is optionally substituted with one or more R8 groups;
R6 is selected from OH, =O, CN, COO-alkyl, aralkyl, heterocyclyl, SO2-alkyl, Salkyl, SO-alkyl, SO2-aryl, COOH, CO-alkyl, CO-aryl, NH2, NH-alkyl, N(alkyl)2, CF3, alkyl and alkoxy;
R7 is H or alkyl, cycloalkyl, aralkyl, alkenyl, cycloalkenyl, heterocyclyl, aryl, C(O)-alkyl, and C(O)-aryl, each of which is optionally substituted with one or more R8 groups;
R8 is selected from the group consisting in H, OH, =O, CN, COO-alkyl, aralkyl, heterocyclyl, SO2-alkyl, Salkyl, SO-alkyl, SO2-aryl, COOH, CO-alkyl, CO-aryl, NH2, NH-alkyl, N(alkyl)2, CF3, alkyl and alkoxy;
Or a prodrug, tautomer, or a pharmaceutically acceptable salt thereof,
a second active agent, which is temozolomide, a prodrug thereof, or a pharmaceutically acceptable salt thereof; and
a pharmaceutically acceptable carrier.

In this object, said composition comprises both active agents within the same formulation.

It is to be understood that said composition may be available when both active agents are suitable for a simultaneous administration in the same dosage form.

In the various objects of the invention defined above, various aspects or embodiments above or below are encompassed, alone or in combination:

The followings are particular embodiments of formula (I):
In one preferred embodiment, Hal is Cl.
In one preferred embodiment, X is —CR1=.
In one preferred embodiment Y is —CR2=.
In another preferred embodiment, Y is N.
In one preferred embodiment Z=—CR3=.
In one preferred embodiment W=—CR4=.
In one preferred embodiment, R1 is H or F, more preferably H.
In one preferred embodiment, R2 is H or F, more preferably H.
In one preferred embodiment, R3 is H or F more preferably H.
In one preferred embodiment, R4 is H, Cl or F preferably H or Cl.
In one preferred embodiment, R3 and R4 are both H.
In one preferred embodiment, R2, R3 and R4 are all H.
In one preferred embodiment, R5 is H, O—(C3-C6)alkyl, O(C2-C6)alkyl-OH, O—(C1-C3)alkyl-S—(C1-C3)alkyl;
In one preferred embodiment, Hal is Cl and R4 is Cl.
In one preferred embodiment, Hal is Cl and R4 is H.
In one especially preferred embodiment, the compound of formula (I) is selected from the following:

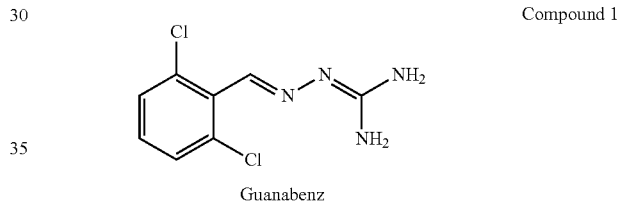

Compound 1

Guanabenz

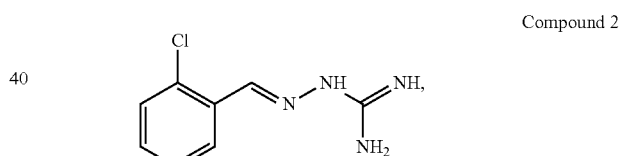

Compound 2

2-(2-chlorobenzylidene)hydrazinecarboximidamide

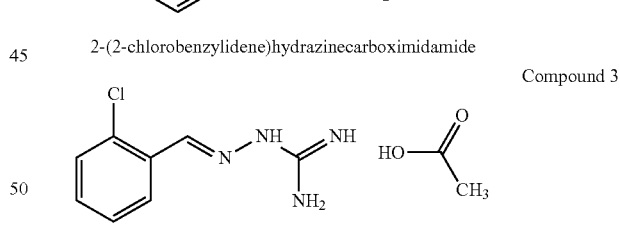

Compound 3

2-(2-chlorobenzylidene)hydrazine carboximidamide acetate

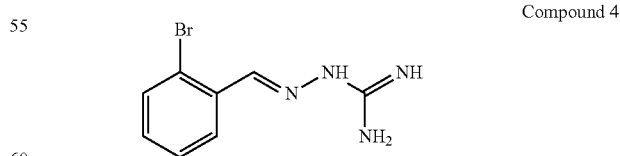

Compound 4

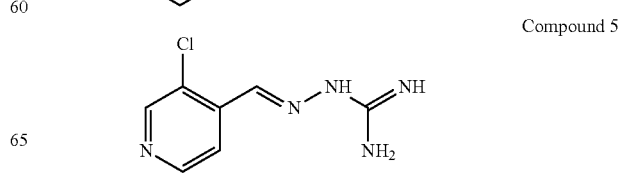

Compound 5

Compound 6

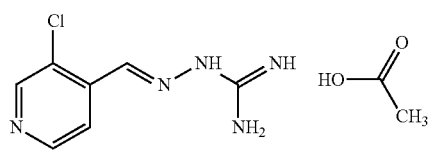

2-[(3-chloropyridin-4-yl)methylidene]hydrazinecarboximidamide acetate

Compound 7

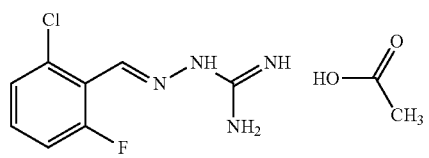

Compound 8

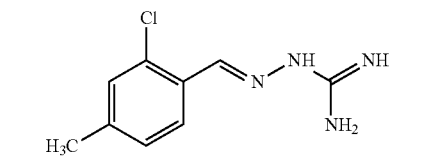

Compound 9

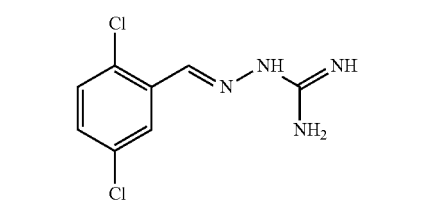

Compound 10

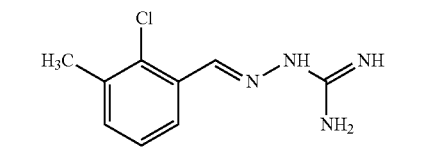

Compound 11

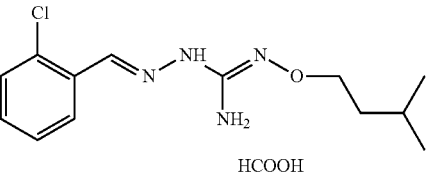

HCOOH 2-(2-chlorobenzyl)-N'-(3-methylbutoxy)hydrazinecarboximidamide formate salt Compound 12

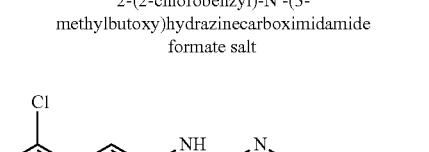

Compound 13

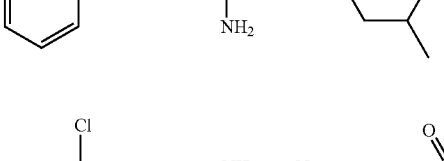

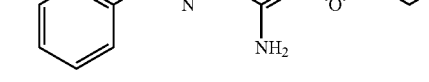

Compound 14

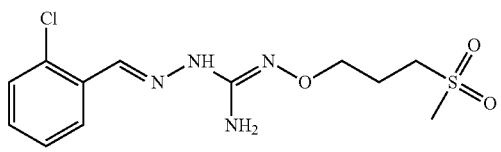

Compound 15

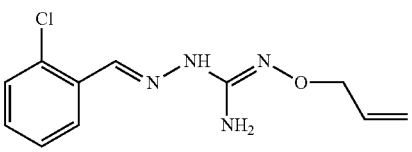

2-(2-chlorobenzylidene)-N'-(prop-2-en-1-yloxy)hydrazine carboximidamide

Compound 16

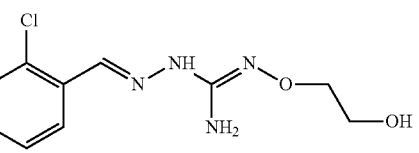

Compound 17

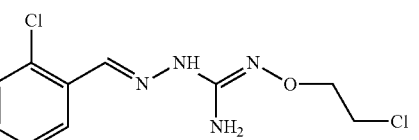

HCl

Compound 18

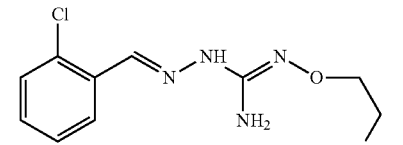

Compound 19

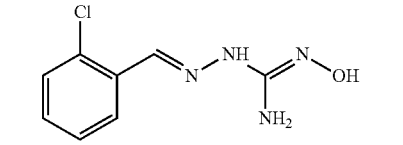

Compound 20

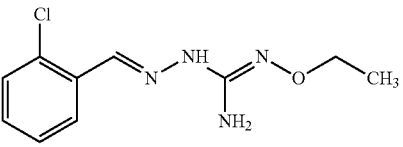

2-(2-chlorobenzylidene)-N'-ethoxyhydrazinecarboximidamide

Compound 21

-continued

Compound 22

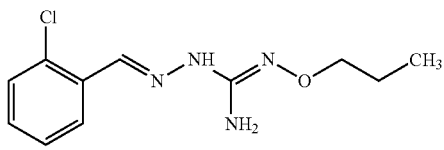

2-(2-chlorobenzylidene)-N-propoxyhydrazinecarboximidamide

Compound 23

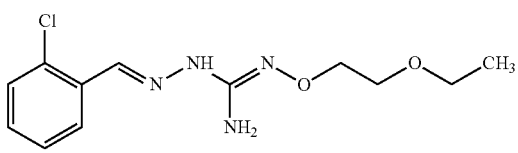

Compound 24

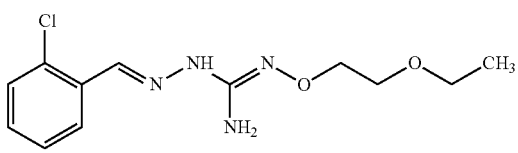

Compound 25

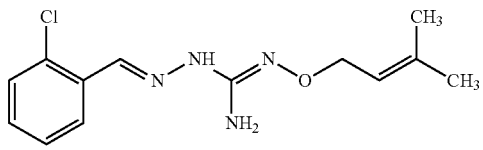

Compound 26

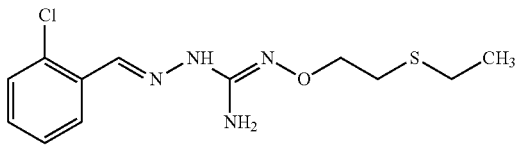

Compound 27

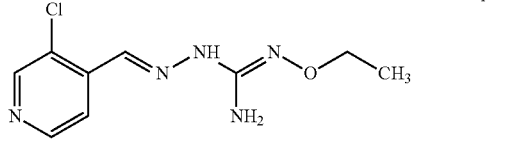

Compound 28

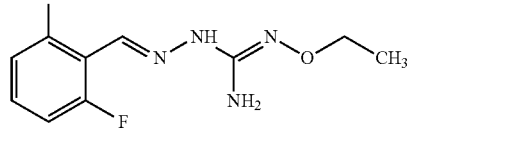

N'-butoxy-2-(2-chlorobenzylidene)hydrazinecarboximidamide

Compound 29

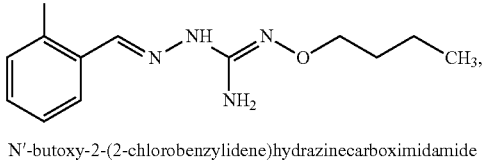

-continued

Compound 30

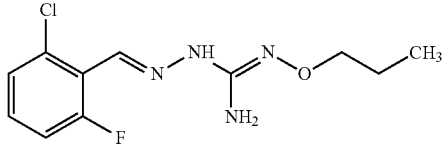

Compound 31

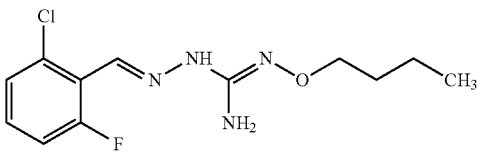

Compound 32

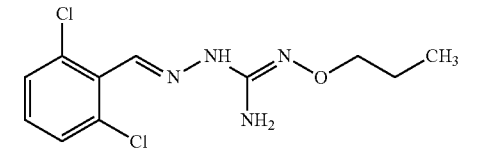

Compound 33

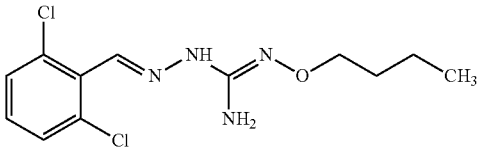

Or a prodrug, tautomer, or a pharmaceutically acceptable salt or free base form thereof.

In an embodiment, the first active agent is guanabenz, a prodrug thereof, or a pharmaceutically acceptable salt thereof.

In an embodiment, the first active agent is 2-(2-chlorobenzylidene)hydrazine carboximidamide or 2-(2-chlorobenzylidene)hydrazine carboximidamide actetate, a prodrug thereof or a pharmaceutically acceptable salt thereof.

In an embodiment, the first active agent is 2-(2-chlorobenzylidene)-N'-ethoxyhydrazinecarboximidamide, a prodrug thereof or a pharmaceutically acceptable salt thereof.

In an embodiment, the first active agent is 2-(2-chlorobenzylidene)-N-propoxyhydrazine carboximidamide, a prodrug thereof or a pharmaceutically acceptable salt thereof.

In an embodiment, the first active agent is N'-butoxy-2-(2-chlorobenzylidene)hydrazinecarboximidamide, a prodrug thereof or a pharmaceutically acceptable salt thereof.

In an embodiment, the first active agent is chosen from 2-[(3-chloropyridin-4-yl)methylidene]hydrazinecarboximidamide acetate, 2-(2-chlorobenzyl)-N'-(3-methylbutoxy)hydrazinecarboximidamide formate salt and 2-(2-chlorobenzylidene)-N'-(prop-2-en-1-yloxy) hydrazine carboximidamide, a prodrug thereof or a pharmaceutically acceptable salt or the free form thereof.

Such combinations are more effective than treatment with either therapy alone. In addition, the present combinations, compositions, formulations, kits, and methods permit a lower dose of one or more pharmaceutically active agents to be administered, than would otherwise be required, to achieve a therapeutic effect thereby reducing adverse effects associated with the dosage administered.

In some embodiments of the method, the compound of formula (I), or a pharmaceutically acceptable salt thereof and the chemotherapeutic agent, or a pharmaceutically acceptable salt thereof, are administered at the same time. In other embodiments, the compound of formula (I), or a pharmaceutically acceptable salt thereof and the chemotherapeutic agent, or a pharmaceutically acceptable salt thereof, are administered at different times. Thus, for example, the TMZ or compounds of formula (I), such guanabenz, 2-(2-chlorobenzylidene)hydrazine carboximidamide, 2-(2-chlorobenzylidene)hydrazine carboximidamide acetate, 2-(2-chlorobenzylidene)-N'-ethoxyhydrazine carboximidamide, 2-(2-chlorobenzylidene)-N-propoxyhydrazine carboximidamide, N'-butoxy-2-(2-chlorobenzylidene) hydrazine carboximidamide, 2-[(3-chloropyridin-4-yl)methylidene]hydrazinecarboximidamide acetate, 2-(2-chlorobenzyl)-N'-(3-methylbutoxy) hydrazinecarboximidamide formate salt and 2-(2-chlorobenzylidene)-N'-(prop-2-en-1-yloxy) hydrazine carboximidamide.
may be administered on the same days or on different days, and/or at the same time or at different times.

Further, the TMZ (or a pharmaceutically acceptable salt thereof) and compounds of formula (I) (or a pharmaceutically acceptable salt thereof) may be administered in combination with any other treatment and/or chemotherapeutic agent. In certain embodiments, the TMZ (or a pharmaceutically acceptable salt thereof) and compounds of formula (I) (or a pharmaceutically acceptable salt thereof) may be administered before and/or after surgery. In other embodiments, the TMZ (or a pharmaceutically acceptable salt thereof) and compounds of formula (I) (or a pharmaceutically acceptable salt thereof) may be administered before, during or after radiation treatment.

BRIEF DESCRIPTION OF DRAWINGS

The accompanying drawings illustrate a disclosed embodiment and serves to explain the principles of the disclosed embodiment. It is understood however that the drawings are designed for purposes of illustration only, and not as a definition of the limits of invention.

DEFINITIONS

Figure 1:
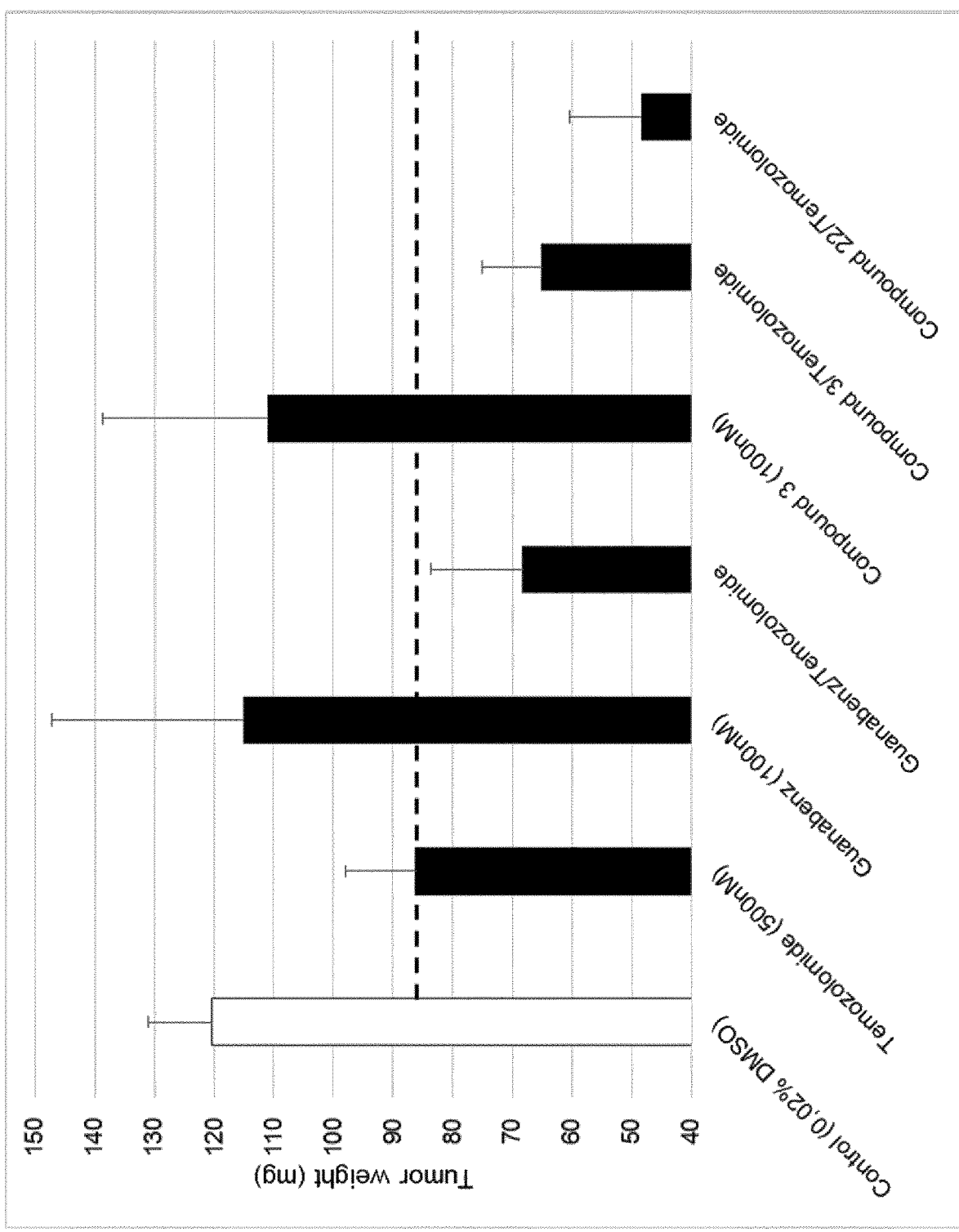
FIG. 1 shows the reduction of GL261 tumor weight upon treatment with temozolomide alone (500 microM) and the synergistic reduction of GL261 tumor weight upon treatment with the combination of compound 3 or 22 or guanabenz and temozolimide as compared to the control. The negative control contains no Temozolomide but DMSO. The compound 3 or guanabenz alone (100 nM) is having no or a weak effect on tumor size reduction.

As used herein, the term «disorder», «disease», «conditions» has the same meaning.

As used herein, the cell proliferative disorder can be any cell proliferative disorder. The phrase "cell proliferative disorder" refers to a neoplasm. That is an abnormal growth of cells or a growth of abnormal cells which reproduce faster than normal. A neoplasm creates an unstructured mass (a tumor) which can be either benign or malignant. The term "benign" refers to a tumor that is non-cancerous, e.g., its cells do not invade surrounding tissues or metastasize to distant sites. The term "malignant" refers to a tumor that is cancerous, and/or metastastic, i.e., invades contiguous tissue or is no longer under normal cellular growth control. Non-limiting examples of cell proliferative disorders that may be treated by the present invention include glioma, melanoma, prostate, lung cancer, breast cancer, ovarian, testicular cancer, gastric cancer, liver, kidney, spleen, bladder, colorectal and/or colon cancer, head and neck, carcinoma, sarcoma, lymphoma or leukemia. In other preferred embodiments, the cell proliferative disorder is glioma.

As used herein, a "glioma" means a tumor or cancer of the glial cells of the nervous system. Gliomas generally start in the brain or the spine. There are three types of glial cells that can give rise to tumors or cancers. The glioma may be an astrocytoma, an oliogodendroglioma, an ependymoma, or a mixture thereof (also called mixed glioma). An astrocytoma is divided into four grades by the World Health Organization. Grade I, or a pilocytic astrocytoma, is characterized by slow growth, with relatively well-defined borders. In an embodiment of the invention, the glioma is an astrocytoma. Grade II, or low-grade astrocytoma, is characterized by slow growth, but with borders that are not well defined. Grade II gliomas rarely spread to other parts of the central nervous system. Grade III, or anaplastic astrocytoma, is characterized by relatively faster and more aggressive growth (in comparison to Grade II), with tumor cells non-uniform in appearance. Grade III gliomas invade neighboring tissues. Grade IV, or glioblastoma, is the most invasive type of glial tumors. Grade IV gliomas grow rapidly and commonly spread to nearby tissue. In one embodiment, the glioma is an anaplastic astrocytoma. In another preferred embodiment, the glioma is a glioblastoma multiforme.

As used herein, a "subject" or a "patient" is a mammal, preferably, a human. In addition to humans, categories of mammals within the scope of the present invention include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population.

As used herein, the terms "ameliorate", "ameliorating" and grammatical variations thereof mean to decrease the severity of the symptoms of a disease in a subject.

As used herein the phrase "preparation of a medicament" includes the use of one or more of the described compounds directly as the medicament in addition to its use in a screening programme for further active agents or in any stage of the manufacture of such a medicament.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "therapeutically effective amount" refers to that amount of the compound being administered which will relieve to some extent one or more of the symptoms of the disease or disorder being treated. As used herein, the phrase "therapeutically effective amount" with respect to the compound of formula (I) and the chemotherapeutic agent means an amount which provides a therapeutic benefit in the treatment or management of a cell proliferative disorder (e.g., glioma, etc.). In preferred embodiments, the therapeutically effective amount of the compound of formula (I), or a pharmaceutically acceptable salt thereof and the chemotherapeutic agent, or a pharmaceutically acceptable salt thereof, means is less that would be required by either therapy alone to achieve a therapeutic effect thereby reducing adverse effects associated with the dosage administered.

As used herein, a "chemotherapeutic agent" is a drug that may be used to treat cancer or tumor, such as, e.g., gliomas. Chemotherapeutic agents may be DNA damaging agents, antimetabolites, anti-microtubule agents, or antibiotic agents. DNA damaging agents include alkylating agents, intercalating agents, and enzyme inhibitors of DNA replication. The chemotherapeutic agent could be any (i) alkylating agent (including nitrogen mustards, ethylenimine derivatives, alkyl sulfonates, nitrosoureas and triazenes); (ii) any DNA intercalating agents or strand breaking agents (including Dactinomycin, doxorubicin, daunorubicin, idarubicin, and mitoxantrone.); (iii) any enzyme inhibitors of DNA replication such as irinotecan, topotecan, amsacrine, etoposide, etoposide phosphate, and teniposide); (iv) antimetabolites (including folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, and decitabine); (v) anti-microtubule agents (including without limitation vinca alkaloids, paclitaxel (Taxol®), docetaxel (Taxotere®), and ixabepilone (Ixempra®)); and (vi) Antibiotic agents include without limitation actinomycin, anthracyclines, valrubicinepirubicin, bleomycin, plicamycin, and mitomycin.

In a preferred embodiment, the chemotherapeutic agent is an alkylating agent, a pharmaceutically acceptable salt thereof, a prodrug thereof, and combinations thereof. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include: Nitrogen mustards, such as Chlorambucil, Cyclophosphamide (Cytotaxan®), Isofamide, Mechlorethamine or mustine, Melphalan, Uramustine or uracil mustard, Chlorambucil, Ifosfamide, Bendamustine; Chlormethine, pipobroman, triethylene-melamine, triethylene thiophosphoramine; Aziridine such as Thiotepa; methanesulphonate esters such as Busulfan; nitroso ureas, such as Carmustine, Lomustine, Streptozocin; platinum complexes, such as Cisplatin, Carboplatin, Nedaplatin, Oxaliplatin, Satraplatin and Triplatin tetranitrate; bioreductive alkylator, such as Mitomycin, and Procarbazine, Dacarbazine, Altretamine and temozolomide (TMZ). In a preferred embodiment, the alkylating agent is temozolomide, a prodrug thereof, or a pharmaceutically acceptable salt thereof.

As used herein, the term "alkyl" includes both saturated straight chain and branched alkyl groups which may be substituted (mono- or poly-) or unsubstituted. Preferably, unless otherwise specified the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Preferably, the alkyl group is unsubstituted.

As used herein, the term "cycloalkyl" refers to a cyclic alkyl group which may be substituted (mono- or poly-) or unsubstituted. Preferably, the cycloalkyl group is a $C_{3-12}$ cycloalkyl group.

As used herein, the term "alkenyl" refers to a group containing one or more carbon-carbon double bonds, which may be branched or unbranched. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. The term "cyclic alkenyl" is to be construed accordingly.

As used herein, the term "aryl" refers to a $C_{6-12}$ aromatic group which may be substituted (mono- or poly-) or unsubstituted. Typical examples include phenyl and naphthyl etc.

As used herein, the term "heterocycle" (also referred to herein as "heterocyclyl" and "heterocyclic") refers to a 4 to 12, preferably 4 to 6 membered saturated, unsaturated or partially unsaturated cyclic group containing one or more heteroatoms selected from N, O and S, and which optionally further contains one or more CO groups. The term "heterocycle" encompasses both heteroaryl groups and heterocycloalkyl groups as defined below.

As used herein, the term "heteroaryl" refers to a 4 to 12 membered aromatic which comprises one or more heteroatoms. Preferably, the heteroaryl group is a 4 to 6 membered aromatic group comprising one or more heteroatoms selected from N, O and S. Suitable heteroaryl groups include pyrrole, pyrazole, pyrimidine, pyrazine, pyridine, quinoline, thiophene, 1,2,3-triazole, 1,2,4-triazole, thiazole, oxazole, iso-thiazole, iso-oxazole, imidazole, furan and the like.

As used herein, the term "heterocycloalkyl" refers to a 3 to 12 membered, preferably 4 to 6 membered cyclic aliphatic group which contains one or more heteroatoms selected from N, O and S. N-containing 5 to 6 membered heterocycloalkyl are preferred. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group. Typical aralkyl groups include benzyl, phenethyl and the like.

As used herein, a "prodrug" means a substance that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester to facilitate transmittal across a cell membrane, but which then is metabolically hydrolyzed to the active entity once inside the cell. Candesartan cilexetil is a non-limiting example of a prodrug (in this case, a prodrug of candesartan). Conventional procedures for the selection and preparation of suitable prodrug derivatives are described, for example, in Design of Prodrugs, (ed. H. Bundgaard, Elsevier, 1985), which is incorporated herein by reference for the purpose of describing procedures and preparation of suitable prodrug derivatives.

As used herein the phrase "pharmaceutically or veterinary acceptable salt" refers to a non-toxic salt prepared from a pharmaceutically or veterinary acceptable acid or base (including inorganic acids or bases, or organic acids or bases).

In a preferred embodiment, the compound of formula (I) is selected from Compounds 1, 2, 3, 6, 11, 15, 20, 22 and 28 as set out above.

Process of Preparation

A further aspect of the invention relates to a process for preparing a compound of formula (I) or pharmaceutically acceptable salts thereof as above described.

Compounds 1 to 10 or pharmaceutically acceptable salts thereof as above described can be prepared according to the following general procedure A:

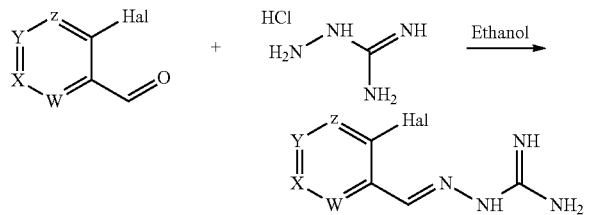

To a solution of benzaldehyde (1 eq.) in ethanol (300 ml) was sequentially added Aminoguanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of NaHCO₃ (700 ml). The resulting precipitate were filtered off under vacuum and washed with water (100 ml). The resulting solid material was titurated with diethylether (2×25 ml) and dried under vacumm to provide the desired substituted aminoguanidine derivative.

Compounds 11 to 33 or pharmaceutically acceptable salts thereof as above described can be prepared according to the following general procedure B, comprising the step of reacting a compound of formula (A) or a tautomer form thereof:

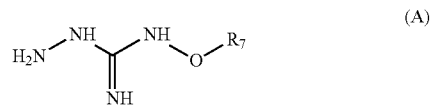

wherein R7 is as defined above, with a compound of formula (B):

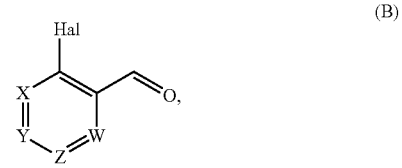

wherein X, Y, Z, W and Hal are as defined above, optionally followed by a step of modifying the R7 group of the compound resulting from the reaction between the compounds of formulae (A) and (B) as above described, into another R7 group.

The coupling reaction between compounds (A) and (B) may be conducted in an organic solvent, such as an alcohol, e.g. ethanol. It may be carried out at a temperature comprised between room temperature and the boiling temperature of the reaction mixture.

The modification reaction of R7 groups may be conducted by application or adaptation of known methods. For example, in the compound obtained following the coupling of (A) and (B), R7 may be an alkyl group substituted by R8 groups: it may thus be desired to substitute R7 groups. Such substitution reactions are generally known. As a representative examples it may be desired to replace R8=OH with R8=halogen in a compound of formula (I). Such reaction may be conducted in the presence of an halogenating agent, such as a chlorinating agent, eg SOCl₂. Typically such a reaction may be conducting in an organic solvent such as dichloromethane. Another representative example is the substitution of R8=halogen with R8=N-containing heterocycle such as pyrrolidine. Such reaction may be conducted in the presence of a base, such as TEA. Typically such a reaction may be conducting in an organic solvent such as THF.

According to an embodiment, the process may further comprise the step of preparing the compound of formula (A) as above defined by reacting a compound of formula (C):

or one of its salts, wherein R7 is as defined above with the S-methylisothiosemicarbazide hydroiodide compound (D):

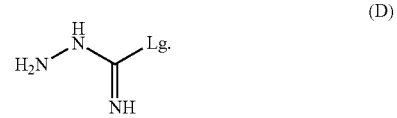

where Lg is a leaving group such as —S-Alkyl, e.g. —S-Methyl, or one of its salts.

Typically, the reaction between the compounds of formulae (C) and (D) may be carried out in a basic aqueous solution, for example in an aqueous solution comprising sodium hydroxide. The coupling reaction between compounds of formulae (C) and (D) may be followed a further step of purification.

In an embodiment, the process may optionally comprise a further step of preparing the compound of formula (C) by reacting a compound of formula (E):

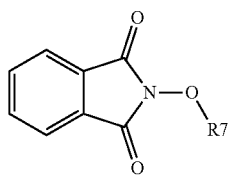

(E)

with a hydrazine derivative compound, for example hydrazine hydrate or methyl hydrazine.

The process of the invention may optionally comprise the step of preparing the compound of formula (E) from a compound of formula (E'):

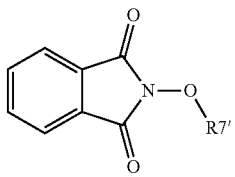

(E')

Where (R7') represents a precursor group of R7.

This reaction may be desired when (E) is not commercially available and it is not practicable to prepare (E) from (F) and (G) as disclosed below.

It may thus be desirable to use a precursor (E') which is to be transformed into (E). A precursor is a group or a compound that may be modified into the desired compound by a substitution, elimination or otherwise derivation chemical reaction.

As an illustrative embodiment, the modification reaction of a R7' into the desired R7 group may be conducted by application or adaptation of known methods. For example, in (E), R7 may be an alkyl group substituted by R8 groups: it may thus be desired to modify R8' groups in (E') into the desired R8' in (E). Such modification reactions are generally known. As a representative example, it may be desired to replace the precursor R8' comprising the group R8'=S (Alkyl) with R8=SO$_2$(Alkyl). Such reaction may be conducted in the presence of MCPBA. Typically such a reaction may be conducting in an organic solvent such as dichloromethane.

The process of the invention may comprise the step of preparing (E) or (E') as appropriate, by reacting a compound (F)

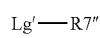

(F)

Where R7" represents either R7 or R7' as defined above, and Lg' represents a leaving group such as a halogen atom or a hydroxyl (OH) group, with N-hydroxyphtalimide (G):

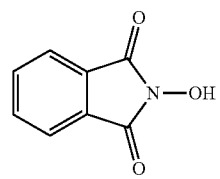

(G)

Generally, the coupling of (F) and (G) may be conducted according to a Gabriel synthesis conditions.

According to an illustrative embodiment, this reaction may be carried out in the presence of a base such as organic or mineral base, typically TEA or K$_2$CO$_3$, or NaOAc, in particular where Lg contains Halogen(s).

According to another illustrative embodiment, the first step may be carried out in the presence of diisopropyl azodicarboxylate and PPh3, in particular where Lg=OH.

Compounds (F), (G), (B) are generally commercially available.

The compounds of formula (D):

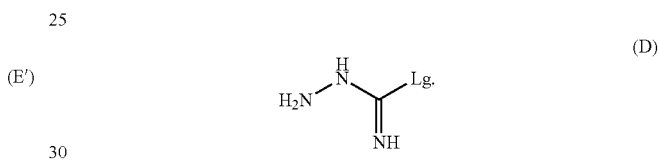

(D)

where Lg is a —S-Alkyl, e.g. —S-Methyl is also part of the invention.

Preferably, the process may also comprise a further step of purification of the compound (I), obtained above with general procedures A and B, In addition to the process disclosed above, the compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, VCH publishers, 1989

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described herein, it may be necessary to protect reactive functional groups, for example hydroxy, amino, imino, thio or carboxy groups, where these are desired in the final product, to avoid their unwanted participation in the reactions.

Conventional protecting groups may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of the invention may also include the additional step of isolating the obtained product of formula (I).

The starting products and/or reagents may be commercially available, or may be readily prepared by the skilled person by applying or adapting the procedures disclosed in the experimental part below.

In the combinations of the invention, the first and second active agents may be administered consecutively, simultaneously or sequentially.

They may also be combined with one or more additional other active agents.

According to the invention, the combination of said first and second active agents may exhibit synergy.

They may also avoid an overlap of major toxicities, mechanism of action and resistance mechanism(s). Furthermore, they may allow the administration of the agents at their maximum tolerated doses with minimum time intervals between such doses. They also may decrease the emergence of resistance.

By studying the inhibitory activity of the first and second active agents, it can be determine the order of administration of the agents, i.e. before, simultaneously, or after delivery.

Pharmaceutical Compositions

For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine. Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal, ocular and sublingual), rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, anti-oxydants, chelating agents, inert gases and the like.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) and/or the chemotherapeutic agent, such as TMZ, in conjunction or association with a pharmaceutically or veterinarily acceptable carrier or vehicle.

Administration

The pharmaceutical compositions of the present invention may be adapted for rectal, nasal, intrabronchial, topical (including buccal, sublingual and ophthalmic administration, in particular for intra-ocular, topical ocular or peri-ocular administration), vaginal or parenteral (including subcutaneous, intramuscular, intravenous, intraarterial and intradermal), epidural, intracerebral or intracerebroventricular route intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active agent per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intra-arterially, intra-thecally, subcutaneously, intra-dermally, intra-peritoneally, intra-ocularly, topical, peri-ocularly or intra-muscularly, and which are prepared from sterile or sterilisable solutions. Injectable forms typically contain between 10-1000 mg, preferably between 10-250 mg, of active agent per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active agent can be incorporated into a cream consisting of an aqueous emulsion of polyethylene glycols or liquid paraffin. The active agent can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation as well as the duration of the treatment. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Generally, the amount of compound of formulae (I), or pharmaceutically acceptable salts thereof, as defined above, to be administered in combination with TMZ is decided on a case by case basis by the attending physician. As a guideline, the extent of the cell proliferative disorder, the body weight, and the age of the patient will be considered, among other factors, when setting an appropriate dose. Of course, this dosage amount will further be modified according to the type of administration of the compound.

To achieve an "effective amount" for therapy, oral or intravenous administration of a compound of general formula (I) is preferred. Typically, the dose will be about 0.01 to about 50 mg/kg, preferably between 0.1 and 20 mg/kg, more preferably between 0.1 and 5 mg/kg, in a manner to maintain the concentration of drug in the plasma at an effective concentration.

The compound of general formula (I) preferably selected from compounds 1, 2, 3, 6, 11, 15, 20, 22, 28, is preferably administered within the range of 1 to 70 mg daily, more preferably 4 to 56 mg daily, even more preferably 8 to 32 mg daily.

The compound of general formula (I) preferably compound 1 is preferably administered with the range of 4 to 64 mg daily, more preferably 8 to 32 mg daily. The compound 1 is preferably administered on escalating dose, beginning with 4 mg twice a day, and increase shall be made with increments of 4 to 8 mg daily at one to two week intervals, depending on the patient's response, up to a maximum of 64 mg daily.

The compounds of general formula (I) may be administered one to several times daily or every two days. Preferably, the compounds of general formula (I) is administered daily.

The precise amount of an inventive compound which is therapeutically effective, and the route by which such compound is best administered, is readily determined by one of ordinary skill in the art by comparing the blood level of the agent to the concentration required to have a therapeutic effect.

In a preferred embodiment compound of general formula (I) preferably selected from compounds 1, 2, 3, 6, 11, 15, 20, 22, 28 is to be administered orally. In another preferred embodiment, compound of general formula (I) preferably selected from compounds 1, 2, 3, 6, 11, 15, 20, 22, 28 is to be administered intravenously.

In a preferred embodiment, the orally administered compounds of the composition are one compound of formula (I) preferably selected from compounds 1, 2, 3, 6, 11, 15, 20, 22, 28 and temozolomide. According to a preferred embodiment, the orally administered compounds of formula (I) is compound 1 (i.e. guanabenz).

In another embodiment, the compounds of the composition are administered intravenously to the patient, in a manner such that the concentration of drug is sufficient to achieve one or more of the therapeutic indications disclosed herein. In a preferred embodiment, the intravenously administered compounds of the composition are one compound of formula (I) preferably selected from compounds 1, 2, 3, 6, 11, 15, 20, 22, 28 and temozolomide.

In another embodiment, at least one compound of the composition is administered orally to the patient and at least one compound of the composition is administered intravenously to the patient, in a manner such that the concentration of drug is sufficient to achieve one or more of the therapeutic indications disclosed herein. Preferably, the orally administered compounds of formula (I) is compound of formula (I) preferably selected from compounds 1, 2, 3, 6, 11, 15, 20, 22, 28 of formula (I) and the intravenously administered compound is temozolomide. According to another embodiment the orally administered compound is temozolomide and the intravenously administered compound is compound of formula (I) preferably selected from compounds 1, 2, 3, 6, 11, 15, 20, 22, 28 of formula (I).

In one embodiment, TMZ may be administered as an oral or intravenous dose in the range of about 150 to about 200 mg/m2 per day for 5 days in a 28-day treatment cycle. In other embodiments, TMZ may also be administered at a dose of 100 mg/m2 per day for 14 days in a 21 day cycle. In other embodiments, TMZ may be administered at a dose of 150 mg/m2 for 7 days in a 14 day cycle. In other embodiments, TMZ may be administered at a dose of 100 mg/m2 per day for 21 days in a 28 day cycle.

In one embodiment, the therapeutically effective amount of TMZ (or pharmaceutically acceptable salt thereof) is either a standard or enhanced dose intensity of TMZ based upon the methylation state of the Q6-methylguanine-DNA methyltransferase (MGMT) gene in a sample obtained from the patient. If the gene (e.g., the promoter region) encoding MGMT in a sample from the patient is methylated, a standard dose intensity of TMZ is administered; however, if the gene encoding MGMT is not methylated (i.e., below the level of detection), an enhanced dose intensity of TMZ is administered to the patient. See U.S. Patent Publication No. 2006/0100188, in particular, exemplary enhanced dose intensities for TMZ are provided in Tables 1 and 2; methods to assess whether or not the MGMT gene is methylated are provided on pages 15-20; and the term "sample" is defined on page 13. The disclosure of U.S. 2006/0100188 is incorporated by reference herein. TMZ may be administered by any suitable route. In a preferred embodiment TMZ is to be administered orally. In another preferred embodiment, TMZ is to be administered intravenously.

The first and second active agents are for simultaneous, separate or sequential use. Preferably, the first and second active agents are for simultaneous use and are administered for substantially the same duration.

As noted above, the above amounts may vary on a case-by-case basis. In some embodiments, TMZ and the compound of formulae (I), or pharmaceutically acceptable salts thereof, as defined above, may be administered in combination with other agents or compounds, including, but not limited another anti-neoplastic agent.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Salts

The compounds of the invention can be present as salts, in particular pharmaceutically and veterinary acceptable salts. Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulfuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1-C_4)$-alkyl- or aryl-sulfonic acids which are unsubstituted or substituted (for example, by a halogen) such as methane- or p-toluene sulfonic acid. Salts which are not pharmaceutically or veterinary acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) and/or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of formula (I) thus also include the tautomer forms of formula:

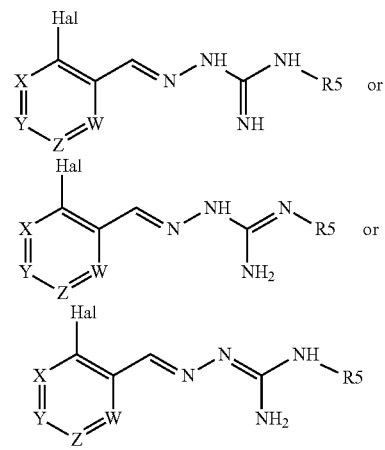

As an illustrative example, a tautomer form of Compound 12 is:

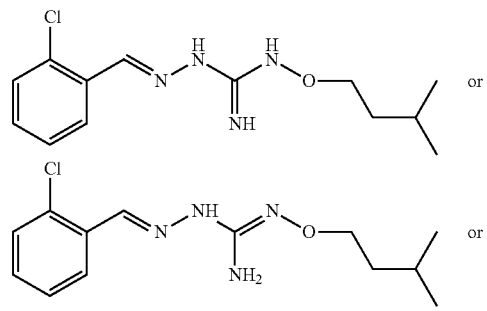

-continued

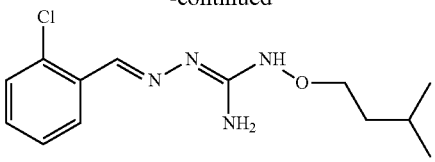

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms as E/Z (Entgegen/Zusammen) isomers. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree). Compounds of formula (I) or (II) thus also include the E and/or Z isomer forms of formula:

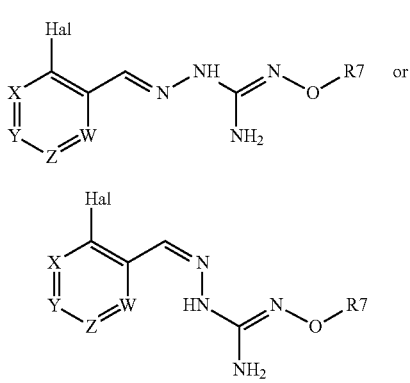

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

EXAMPLES

The present invention is further described with reference to the following non-limiting examples.

1—Methods & Materials 1.1—Preparation of the Compounds According to the Present Invention Compound 1: guanabenz or 2-(2,6-dichlorobenzylidene)hydrazine carboximidamide was purchased from Sigma-Aldrich ref: G110.

Compound 4 was purchased from Chembridge ref: 5173161.

The following compounds were prepared according general procedure A:

Compound 2:
2-(2-chlorobenzylidene)hydrazinecarboximidamide

Prepared following general procedure A from 2-chlorobenzaldehyde (10 g) to give 11.1 g of desired compound (yield: 79.6%). $^1$H-NMR (DMSO-d$_6$): δ (ppm) 5.66 (s, 2H); 6.05 (s broad, 2H); 7.27 (m, 2H); 7.40 (m, 1H); 8.14 (dd, 1H); 8.27 (s, 1H); MS (ESI+): m/z=197.2 [M+H]$^+$.

Compound 3:
2-(2-chlorobenzylidene)hydrazinecarboximidamide
Acetate

To a suspension of 2-chlorobenzaldehyde (30.0 g) and Aminoguanidine bicarbonate (29.0 g) in Methanol (450 ml)

was added Acetic acid (30 ml) at 25° C. The reaction mixture was stirred at 70° C. for 30 minutes. Reaction completion was monitored on TLC using Dichloromethane/Methanol (8/2) as mobile phase. After completion of reaction, the reaction mixture was allowed to cool down to 25° C. and concentrated under vacuum. The residue was suspended in methanol (250 ml) and insoluble material was removed by flirtation. The resulting filtrate was concentrated under vacuum and the above mentioned process (suspension in methanol+filtration) was repeated for three more times. Then, the solid material was triturated with diethyl ether (3×100 ml) and dried under vacuum to provide 46.0 g of 2-(2-chlorobenzylidene)hydrazinecarboximidamide acetate Salt (yield: 84.2%) LC-MS: m/z=197.2 (M+H). $^1$H-NMR (DMSO-d$_6$): δ (ppm) 1.81 (s, 3H), 7.12 (m, 4H); 7.34 (m, 2H); 7.46 (m, 1H); 8.22 (m, 1H); 8.36 (s, 1H); LC-MS: m/z=197.2 [M+H]$^+$.

Compound 5: 2-[(3-chloropyridin-4-yl)methylidene] hydrazinecarboximidamide

Prepared following general procedure A from 2-chlorobenzaldehyde (0.5 g) to give 0.16 g of desired compound (yield: 23%). $^1$H-NMR (DMSO-d$_6$): δ (ppm) 6.00 (s broad, 2H); 6.32 (s broad, 2H); 8.10 (d, 1H); 8.14 (s, 1H); 8.35 (dd, 1H); 8.52 (s, 1H); MS (ESI+): m/z=198.0 [M+H]$^+$.

Compound 6: 2-[(3-chloropyridin-4-yl)methylidene] hydrazinecarboximidamide Acetate To a suspension of 3-chloroisonicotinaldehyde (2.0 g) and aminoguanidine bicarbonate (2.12 g) in methanol (28 ml) was added acetic acid (2 ml) at 25° C. The reaction mixture was stirred at 70° C. for ~2 hours. Reaction completion was monitored on TLC using Dichloromethane/Methanol (8/2) as mobile phase. After completion of reaction, the crude mixture were allowed to cool down to 25° C. and concentrated under vacuum. The solid material was triturated with methanol:diethyl ether (9:1) (4×50 ml) and dried under vacuum to 2.0 g of 2-[(3-chloropyridin-4-yl)methylidene] hydrazinecarboximidamide acetate salt (yield: 55.1%). $^1$H-NMR (DMSO-d$_6$): δ (ppm) 6.01 (brs, 2H); 6.48 (m, 4H); 8.12 (d, 1H); 8.16 (s, 1H); 8.38 (dd, 1H); 8.54 (s, 1H); MS (ESI+): m/z=198.1 [M+H]$^+$.

Compound 7: 2-(2-chloro-6-fluorobenzylidene)hydrazinecarboximidamide Acetate

To a suspension of 2-chloro-6-fluorobenzaldehyde (1.5 g) and aminoguanidine bicarbonate (1.29 g) in methanol (22 ml) was added acetic acid (1.5 ml) at 25° C. The reaction mixture was stirred at 70° C. for ~1 hour. Reaction completion was monitored on TLC using Dichloromethane/Methanol (8/2) as mobile phase. After completion of reaction, the mixture was allowed to cool down to 25° C. and concentrated under vacuum. The resulting solid material was triturated with methanol:diethyl ether (9:1) (3×50 ml) and dried under vacuum to give 2.2 g 2-(2-chloro-6-fluorobenzylidene)hydrazinecarboximidamide acetate Salt (yield: 84.8%). $^1$H-NMR (DMSO-d$_6$): δ (ppm) 1.89 (s, 3H), 6.13 (s broad, 4H); 7.24 (m, 1H); 7.33 (m, 2H) 8.17 (s, 1H); MS (ESI+): m/z=215.1 [M+H]$^+$.

Compound 8: 2-(2-chloro-4-methylbenzylidene) hydrazinecarboximidamide

Prepared following general procedure A from 2-chloro-4-methylbenzaldehyde (0.2 g) to give 255 mg of desired compound (yield: 93.8%). $^1$H-NMR (DMSO-d$_6$): δ (ppm) 2.29 (s, 3H); 5.60 (s broad, 2H); 6.00 (s broad, 2H); 7.10 (d, 2H); 7.27 (s, 1H); 8.02 (d, 1H); 8.24 (s, 1H); MS (ESI+): m/z=210.9 [M+H]$^+$.

Compound 9: 2-(2-chloro-5-methylbenzylidene) hydrazinecarboximidamide

Prepared following general procedure A from 2-chloro-5-methylbenzaldehyde (0.2 g) to give 156 mg of desired compound (yield: 57.4%). $^1$H-NMR (DMSO-d$_6$): δ (ppm) 2.30 (s, 3H); 5.64 (s broad, 2H); 6.06 (s broad, 2H); 7.07 (d, 2H); 7.27 (d, 1H); 7.97 (s, 1H); 8.24 (s, 1H); MS (ESI+): m/z=210.9 [M+H]$^+$.

Compound 10: 2-(2-chloro-3-methylbenzylidene) hydrazinecarboximidamide

Prepared following general procedure A from 2-chloro-3-methylbenzaldehyde (0.2 g) to give 226 mg of desired compound (yield: 83.1%). $^1$H-NMR (DMSO-d$_6$): δ (ppm) 2.17 (s, 3H); 5.64 (s broad, 2H); 6.03 (s broad, 2H); 7.18 (t, 2H); 7.24 (d, 1H); 7.99 (s, 1H); 8.37 (s, 1H); MS (ESI+): m/z=210.9 [M+H]$^+$.

Compounds 11 & 12: Preparation of 2-(2-chlorobenzyl)-N'-(3-methylbutoxy)hydrazinecarboximidamide Formate Salt (Compound 11) and 2-(2-chlorobenzyl)-N'-(3-methylbutoxy) hydrazinecarboximidamide (Compound 12)

2-(3-methylbutoxy)-1H-isoindole-1,3(2H)-dione (I-1)

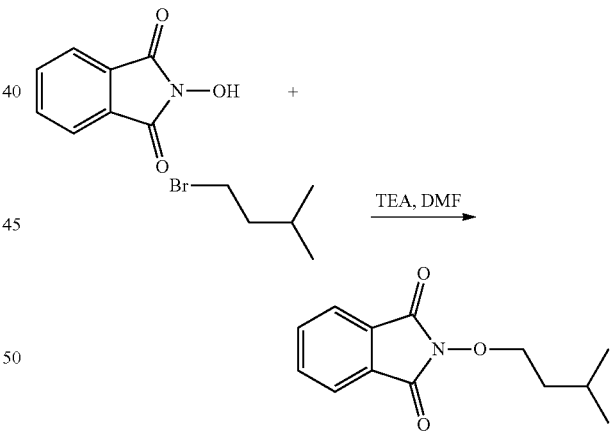

Triethylamine (49.58 g) was added drop wise to a stirred solution of N-Hydroxyphthalimide (40 g) and 1-bromo-3-methyl butane (37.4 g) in DMF (600 ml) at room temperature. The reaction mixture was stirred at 70° C. for 18 hours. The reaction mixture was allowed to cool to room temperature. The mixture was concentrated under reduced pressure and the residue thus obtained was suspended in cold water (1000 ml). The resulting suspension was stirred well for some time and the solid was filtered off under reduced pressure. The solid was further washed with demineralized water (200 ml) and hexane (100 ml). The resulting solid was dried under reduced pressure to get a crude material which was purified by column chromatography using silica gel.

The desired product eluted at around 2% Methanol in dichloromethane. Evaporation of pure product fractions gave 50.0 g of 2-(3-methylbutoxy)-1H-isoindole-1,3(2H)-dione (Yield: 87.4%). $^1$H-NMR (DMSO-d6): δ (ppm) 0.93 (d, 6H), 1.57 (q, 2H), 1.82 (m, 1H), 4.16 (t, 2H), 7.86 (s, 4H); LC-MS: m/z=234.25 (M+H).

1-(amino-oxy)-3-methylbutane Hydrochloride (I-2)

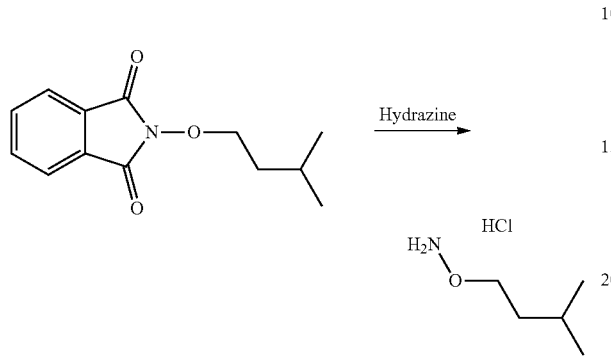

Hydrazine hydrate (12.8 g) was added drop-wise to a stirred solution of 2-(3-methylbutoxy)-1H-isoindole-1,3(2H)-dione (45 g) in methanol (600 ml) at room temperature. The reaction mixture was stirred at the same temperature for 24 hours. The reaction mixture was filtered off to remove the insoluble by-product and the resulting filtrate was concentrated under reduced pressure to get a crude material which was purified by column chromatography using silica gel. The desired product eluted at around 1% Methanol in dichloromethane. Evaporation of pure product fractions gave the desired intermediate as free base which was converted as hydrochloride salt using 4M HCl in 1,4-dioxane, to get 3.3 g of 1-(aminooxy)-3-methylbutane hydrochloride. $^1$H-NMR (DMSO-d6): δ (ppm) 0.89 (d, 6H), 1.46 (q, 2H), 1.65 (m, 1H), 4.01 (t, 2H), 10.84 (s, 3H).

N'-(3-methylbutoxy)hydrazinecarboximidamide (I-3)

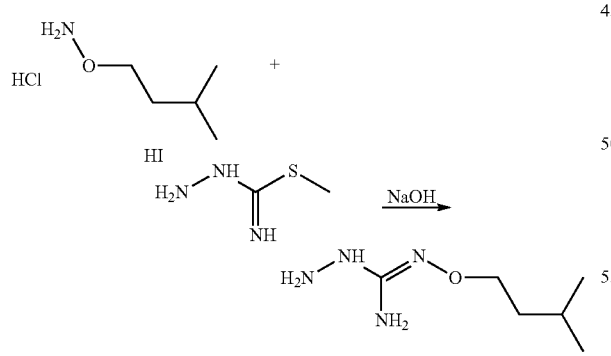

2N NaOH solution (3.6 ml) was added drop wise to a stirred solution of 1-(amino-oxy)-3-methylbutane hydrochloride (1.2 g) and s-methylisothiosemicarbazide hydroiodide (2.02 g) in water (3.6 ml) at room temperature and was stirred for 48 hours. Then, the reaction mixtures was concentrated under reduced pressure and the residue was azeotroped with methanol (5 ml). The resulting residue was suspended in ethanol (10 ml) and insoluble inorganic salts were removed by filtration. The filtrate was directly used for the next step without any further processing. N'-(3-methylbutoxy)hydrazinecarboximidamide was confirmed by LCMS analysis. LC-MS: m/z=161.5 (M+H).

2-(2-chlorobenzyl)-N'-(3-methylbutoxy)hydrazinecarboximidamide Formate Salt (Compound 11)

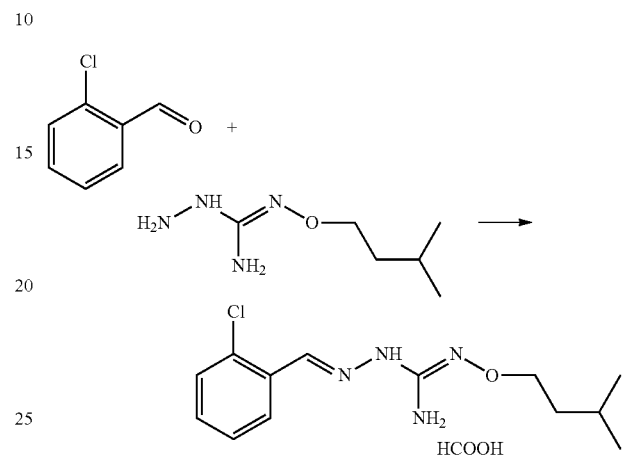

2-chlorobenzaldehyde (1.81 g) was added drop wise to the filtrate which contain N'-(3-methylbutoxy)hydrazinecarboximidamide at room temperature and was stirred for 2 hours. Then, the reaction mixture was concentrated under reduced pressure and the residue thus obtained was further purified by Prep HPLC using 0.1% HCOOH/water/MeCN to give 0.27 g of 2-(2-chlorobenzyl)-N'-(3-methylbutoxy)hydrazinecarboximidamide as formate salt (Yield: 13.1%). $^1$H-NMR (DMSO-d6): δ (ppm) 0.88 (d, 6H), 1.48 (q, 2H), 1.68 (m, 1H), 3.75 (t, 2H), 7.32 (m, 2H), 7.44 (m, 2H), 8.10 (m, 1H), 8.14 (m, 1H), 8.25 (m, 1H), 11.80 (s broad, 2H). LC-MS: m/z=282.88 (M+H).

2-(2-chlorobenzyl)-N'-(3-methylbutoxy)hydrazinecarboximidamide (Compound 12)

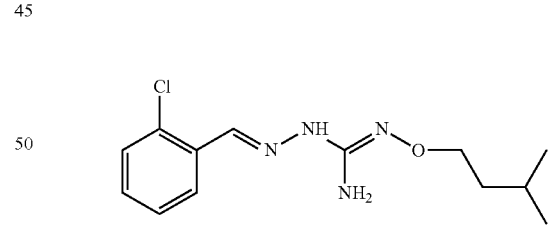

2-(2-chlorobenzyl)-N'-(3-methylbutoxy)hydrazinecarboximidamide formate salt (220 mg) was dissolved in water and was basified by saturated NaHCO$_3$ aqueous solution. The basic aqueous solution was extracted with Dichloromethane and the organic layer was washed with water, dried over sodium sulphate and evaporated under reduced pressure to give 180 mg of 2-(2-chlorobenzyl)-N'-(3-methylbutoxy)hydrazinecarboximidamide as free base (Yield: 95%). $^1$H-NMR (DMSO-d6): δ (ppm) 0.89 (d, 6H), 1.49 (q, 2H), 1.69 (m, 1H), 3.75 (t, 2H), 5.73 (s broad, 2H), 7.30 (m, 2H), 7.44 (m, 1H), 8.11 (m, 1H), 8.15 (m, 1H), 10.48 (s broad, 1H). LC-MS: m/z=282.82 (M+H).

Compound 13: Preparation of 2-(2-chlorobenzylidene)-N'-[2-(methylsulfonyl)ethoxy]hydrazinecarboximidamide 2-[2-(methylsulfanyl)ethoxy]-1H-isoindole-1,3(2H)-dione (I-4)

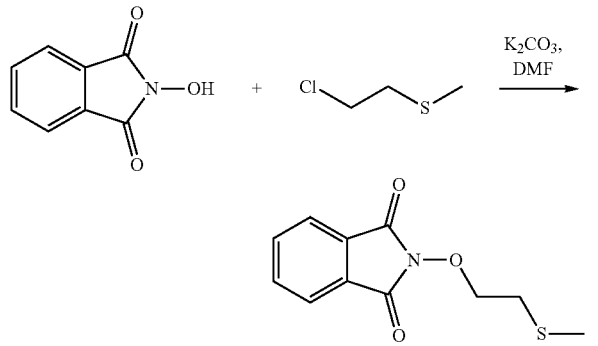

2-chloroethyl methyl sulfide (10.1 g) was added dropwise to a stirred solution of N-Hydroxyphthalimide (12.5 g), potassium iodide (2.5 g) and potassium carbonate (21.1 g) in DMF (150 ml) at room temperature and was stirred at the 80° C. for 18 hours. The reaction mixture was allowed to cool to room temperature and was dumped in 500 ml of cold water. Then, the solid thus obtained was filtered off under reduced pressure. The resulting solid was dried under reduced pressure to give 9.7 g of 2-[2-(methylsulfanyl)ethoxy]-1H-isoindole-1,3(2H)-dione (Yield: 52.8%) and was used for the next step without any further processing. $^1$H-NMR (DMSO-d6): δ (ppm) 2.16 (s, 3H), 2.84 (t, 2H), 4.29 (t, 2H), 7.87 (s, 4H). LC-MS: m/z=238.4 (M+H).

2-[2-(methylsulfonyl)ethoxy]-1H-isoindole-1,3(2H)-dione (I-5)

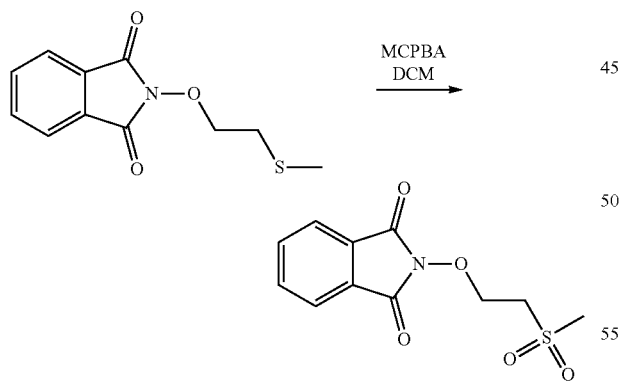

m-CPBA (11 g) was added portion wise to a stirred solution of 2-[2-(methylsulfanyl)ethoxy]-1H-isoindole-1,3 (2H)-dione (9.6 g) in dichloromethane (100 ml) at room temperature and was stirred at room temperature for 6 hours. The crude was concentrated under reduced pressure and the resulting residue was suspended in saturated NaHCO$_3$ solution (100 ml) and stirred for 30 minutes. The resulting solid was filtered off under reduced pressure and washed with water (50 ml) and was dried under reduced pressure to give 9.0 g of 2-[2-(methylsulfonyl)ethoxy]-1H-isoindole-1,3 (2H)-dione (Yield: 82.6%) and was used for the next step without any further processing. $^1$H-NMR (DMSO-d6): δ (ppm) 3.15 (s, 3H), 3.66 (t, 2H), 4.54 (t, 2H), 7.88 (s, 4H). LC-MS: m/z=270.3 (M+H).

1-(aminooxy)-2-(methylsulfonyl)ethane Hydrochloride (I-6)

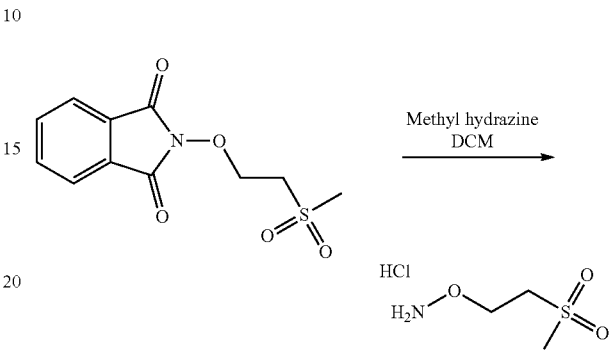

85% methyl hydrazine (2.0 g) was added drop wise to a stirred suspension of 2-[2-(methylsulfonyl)ethoxy]-1H-isoindole-1,3(2H)-dione (9.0 g) in dichloromethane (100 ml) at room temperature and was stirred for 6 hours. Then the reaction mixture was filtered off under reduced pressure to remove insoluble by-product. The resulting filtrate was concentrated under reduced pressure at lower temperature. The residue was suspended in 1N HCl (100 ml) and extracted by ethyl acetate (3×250 ml). The resulting aqueous solution containing the desired product was concentrated under reduced pressure to give white solid which was further triturated with diethyl ether and dried under reduced pressure to give 4.0 g of 1-(aminooxy)-2-(methylsulfonyl)ethane hydrochloride (Yield: 68.3%). $^1$H-NMR (DMSO-d6): δ (ppm) 3.04 (s, 3H), 3.60 (t, 2H), 4.38 (t, 2H), 10.09 (s broad, 2H). LC-MS: m/z=270.3 (M+H).

N'-[2-(methylsulfonyl)ethoxy]hydrazinecarboximidamide (I-7)

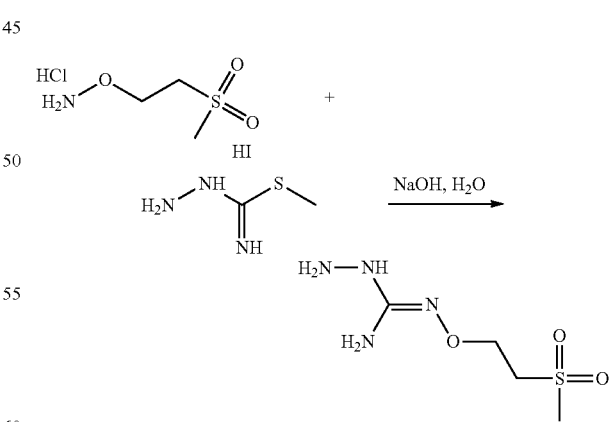

2N NaOH solution (4.28 ml) was added drop wise to a stirred solution of 1-(aminooxy)-2-(methylsulfonyl)ethane hydrochloride (1.5 g) and s-methylisothiosemicarbazide hydroiodide (1.99 g) in water (4.5 ml) at room temperature and was stirred for 48 hours. Then, the reaction mixture was concentrated under reduced pressure and the residue was azeotroped with methanol (5 ml). The resulting material was suspended in ethanol (10 ml) and insoluble inorganic salts were removed by filtration. The resulting filtrate which contain N'-[2-(methylsulfonyl)ethoxy]hydrazinecarboximidamide was directly used for the next step without any further processing.

2-(2-chlorobenzylidene)-N'-[2-(methylsulfonyl)ethoxy]hydrazinecarboximidamide (Compound 13)

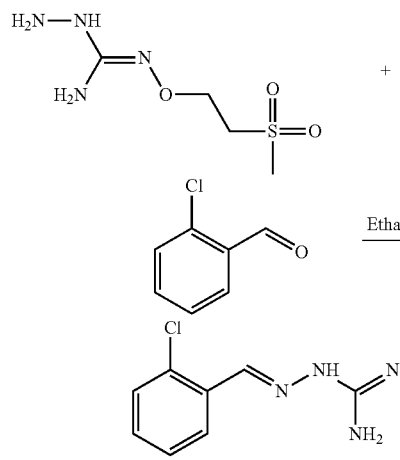

2-chlorobenzaldehyde (1.32 g) was added drop wise to the filtrate containing N'-[2-(methylsulfonyl)ethoxy]hydrazinecarboximidamide at room temperature. The mixture was stirred at room temperature for 2 hours. The reaction mixture was concentrated under reduced pressure and the residue thus obtained was further purified by Prep HPLC using 0.1% $NH_3$/water/MeCN to give 20 mg of 2-(2-chlorobenzylidene)-N'-[2-(methylsulfonyl)ethoxy]hydrazinecarboximidamide (Yield: 0.7% for 2 steps). $^1$H-NMR (DMSO-d6): δ (ppm) 3.03 (s, 3H), 3.45 (m, 2H), 4.12 (m, 2H), 6.11 (s broad, 2H), 7.40 (m, 2H), 7.44 (m, 1H), 8.15 (m, 1H), 8.26 (s broad, 1H), 10.48 (s, 1H). LC-MS: m/z=318.83 (M+H).

Compound 14: 2-(2-chlorobenzylidene)-N'-[3-(methylsulfonyl)propoxy]hydrazinecarboximidamide 2-[3-(methylsulfanyl)propoxy]-1H-isoindole-1,3(2H)-dione (I-8)

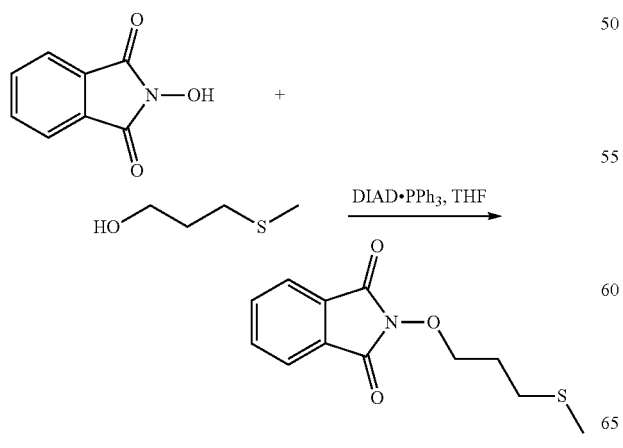

Diisopropyl azodicarboxylate (77.92 ml) was added drop wise to a stirred solution of N-Hydroxyphthalimide (36.8 g), 3-(methylsulfanyl)-1-propanol (30 g) and triphenylphosphine (37.1 g) in anhydrous THF (600 ml) under nitrogen atmosphere at 0° C. The reaction mixture was stirred at 0° C. for 30 minutes and then it was allowed to warm to room temperature and was stirred for 18 hours. Then, the reaction mixture was concentrated under reduced pressure to get a crude material which was purified by column chromatography using silica gel. The desired product eluted at 4% ethyl acetate in hexane. Evaporation of pure product fractions gave 30 g of 2-[3-(methylsulfanyl)propoxy]-1H-isoindole-1,3(2H)-dione (Yield: 42.2%). $^1$H-NMR (DMSO-d6): δ (ppm) 1.94 (q, 2H), 2.07 (s, 3H), 2.67 (t, 2H), 4.23 (t, 2H), 7.87 (s, 4H). LC-MS: m/z=252.4 (M+H).

2-[3-(methylsulfonyl)propoxy]-1H-isoindole-1,3(2H)-dione (I-9)

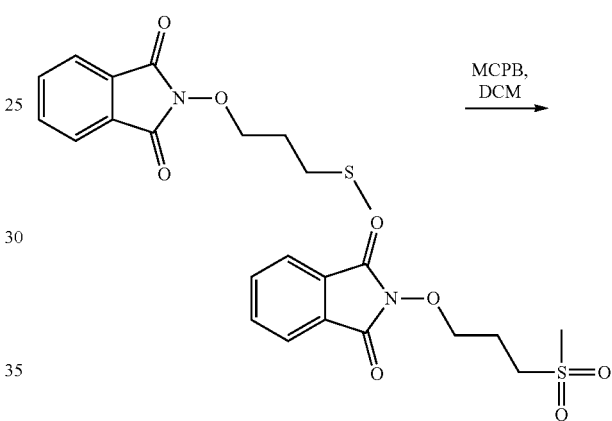

m-CPBA (61.89 g) was added portion wise to a stirred solution of 2-[3-(methylsulfanyl)propoxy]-1H-isoindole-1,3(2H)-dione (30.0 g) in dichloromethane (550 ml) at room temperature. The mixture was stirred at the room temperature for 5 hours. Then, the reaction mixtures was concentrated under reduced pressure to get a crude material which was suspended in saturated $NaHCO_3$ solution (250 ml) and stirred well for 30 minutes. The resulting solid was filtered off under reduced pressure and washed with water (100 ml). The solid was dried under reduced pressure to give 22 g of 2-[3-(methylsulfonyl)propoxy]-1H-isoindole-1,3(2H)-dione (yield: 65%). $^1$H-NMR (CDCl3): δ (ppm) 2.32 (m, 2H), 3.00 (s, 3H), 3.50 (t, 2H), 4.39 (t, 2H), 7.83 (m, 4H). LC-MS: m/z=283.9 (M+H).

1-(aminooxy)-3-(methylsulfonyl)propane Hydrochloride (I-10)

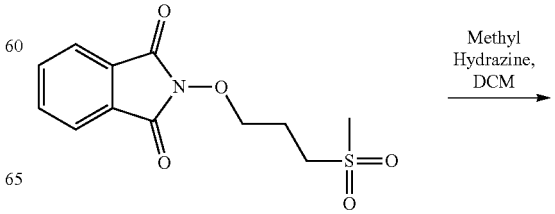

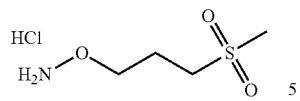

85% methyl hydrazine (4.2 g) was added drop wise to a stirred suspension of 2-[3-(methylsulfonyl)propoxy]-1H-isoindole-1,3(2H)-dione (20 g) in dichloromethane (300 ml) at room temperature and was stirred for 6 hours. Then, the solution was filtered off under reduced pressure to remove the insoluble by-product. The resulting filtrate was concentrated under reduced pressure at low temperature. The residue was suspended in 1N HCl (200 ml) and extracted by ethyl acetate (3×500 ml) to remove undesired impurities. The resulting aqueous solution was concentrated under reduced pressure to give a white solid which was further triturated with diethyl ether and dried under reduced pressure to give 8.0 g of 1-(aminooxy)-3-(methylsulfonyl)propane hydrochloride (Yield: 59.8%). $^1$H-NMR (DMSO-d6): δ (ppm) 2.04 (m, 2H), 3.02 (s, 3H), 3.19 (t, 2H), 4.12 (t, 2H), 11.06 (s broad, 3H).

N'-[3-(methylsulfonyl)propoxy]hydrazinecarboximidamide (I-11)

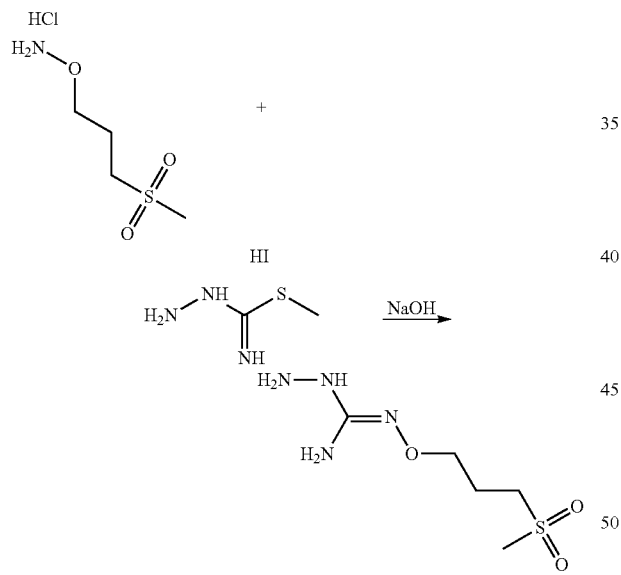

2N NaOH solution (5.28 ml) was added drop wise to a stirred solution of 1-(aminooxy)-3-(methylsulfonyl)propane hydrochloride (2.0 g) and s-methylisothiosemicarbazide hydroiodide (2.46 g) in water (6.0 ml) at room temperature. The reaction mixture was stirred at the room temperature for 24 hours. Formation of N'-[3-(methylsulfonyl)propoxy]hydrazinecarboximidamide was confirmed by LCMS analysis. Then, the mixture was concentrated under reduced pressure and the residue was azeotroped with methanol (15 ml). The resulting material was suspended in ethanol (15 ml) and the insoluble inorganic salts were removed by filtration. The filtrate was directly used for the next step without any further processing. LC-MS: m/z=210.8 (M+H).

2-(2-chlorobenzylidene)-N'-[3-(methylsulfonyl)propoxy]hydrazinecarboximidamide (Compound 14)

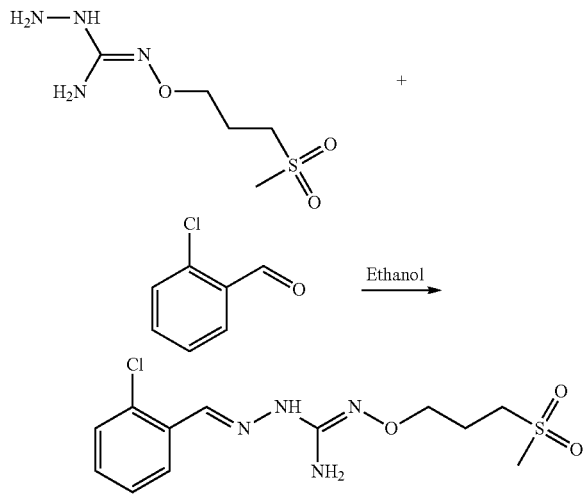

2-chlorobenzaldehyde (1.62 g) was added drop wise to the filtrate containing N'-[3-(methylsulfonyl)propoxy]hydrazinecarboximidamide at room temperature. The resulting reaction mixture was stirred at the same temperature for 2 hours. The crude was concentrated under reduced pressure and the residue thus obtained was further purified by Prep HPLC using 0.1% NH$_3$/water/MeCN. After purification, the material was stirred in saturated NaHCO$_3$ solution and the resulting solid was filtered off under reduced pressure and washed with water and dried to give 0.14 g of pure 2-(2-chlorobenzylidene)-N'-[3-(methylsulfonyl)propoxy]hydrazinecarboximidamide (Yield: 4% for 2 steps). $^1$H-NMR (DMSO-d6): δ (ppm) 2.01 (m, 2H), 2.98 (s, 3H), 3.24 (t, 2H), 3.82 (t, 2H), 5.90 (s, 2H), 7.31 (m, 2H), 7.43 (d, 1H), 8.13 (m, 2H), 10.48 (s, 1H). LC-MS: m/z=333.5 (M+H).

Compound 15: 2-(2-chlorobenzylidene)-N'-(prop-2-en-1-yloxy) Hydrazine Carboximidamide

N'-(prop-2-en-1-yloxy)hydrazinecarboximidamide (I-12)

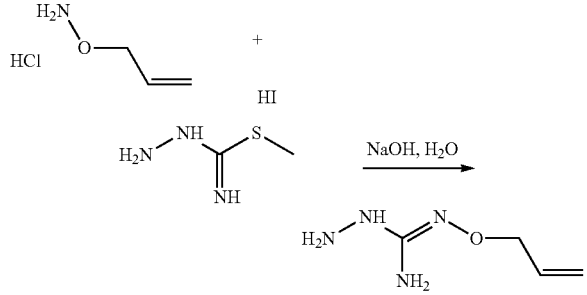

2N NaOH solution (6.8 ml) was added drop wise to a stirred solution of O-Allylhydroxylamine hydrochloride (1.5 g) and s-methylisothiosemicarbazide hydroiodide (3.22 g) in water (4.2 ml) at room temperature. The reaction mixture was stirred at room temperature for 48 hours. Formation of intermediate I-12 N'-(prop-2-en-1-yloxy)hydrazinecarboximidamide was confirmed by LCMS analysis. Then, the mixture was concentrated under reduced pressure and the residue was azeotroped with methanol (5 ml). The resulting material was suspended in ethanol (10 ml) and the insoluble inorganic salts were removed by filtration. The filtrate was directly used for the next step without any further processing. LC-MS: m/z=130.6 (M+H).

2-(2-chlorobenzylidene)-N'-(prop-2-en-1-yloxy) hydrazine Carboximidamide (Compound 15)

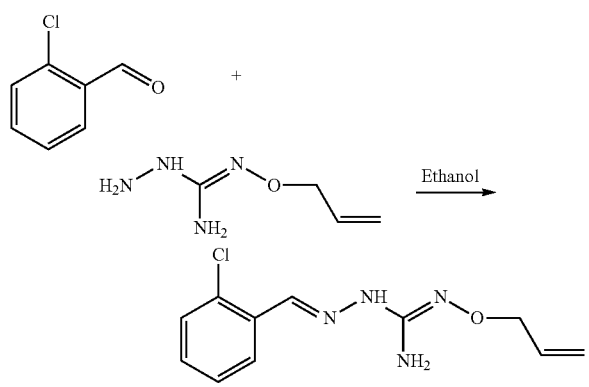

2-chlorobenzaldehyde (1.9 g) was added drop wise to the filtrate containing N'-(prop-2-en-1-yloxy)hydrazinecarboximidamide at room temperature and was stirred for 2 hours. The reaction mixture was concentrated under reduced pressure and the residue thus obtained was further purified by Prep HPLC using 0.1% HCOOH/water/MeCN to give 0.25 g of 2-(2-chlorobenzylidene)-N'-(prop-2-en-1-yloxy)hydrazinecarboximidamide (Yield: 6.1% for 2 steps. $^1$H-NMR (DMSO-d6): δ (ppm) 3.17 (s, 1H), 4.23 (m, 2H), 5.82 (s broad, 2H), 5.98 (m, 1H), 7.37 (m, 2H), 8.15 (m, 3H). LC-MS: m/z=252.8 (M+H).

Compound 16:
2-(2-chlorobenzylidene)-N'-(2-hydroxyethoxy) Hydrazine Carboximidamide 2-(2-hydroxyethoxy)-1H-isoindole-1,3(2H)-dione (I-13)

2-Bromotehanol (13.26 ml) was added drop wise to a stirred solution of N-Hydroxyphthalimide (10.0 g) and Sodium acetate (25.14 g) in DMF (50 ml) at room temperature. The resulting reaction mixture was stirred at 80° C. for 1.5 hours. The reaction mixture was allowed to cool to room temperature and was dumped in 500 ml of cold water and the product was extracted by ethyl acetate (2×400 ml). The resulting organic layer were combined and distilled under vacuum. The residue was stirred in cold water and the resulting solid was filtered off under vacuum. The solid was dried under reduced pressure to give 6.0 g of 2-(2-hydroxyethoxy)-1H-isoindole-1,3(2H)-dione (Yield: 47.3%) which were used for the next step without any further processing. $^1$H-NMR (DMSO-d6): δ (ppm) 3.70 (q, 2H), 4.18 (t, 2H), 4.83 (t, 1H), 7.87 (s, 4H). LC-MS: m/z=208.34 (M+H).

2-(aminooxy)ethanol Hydrochloride (I-14)

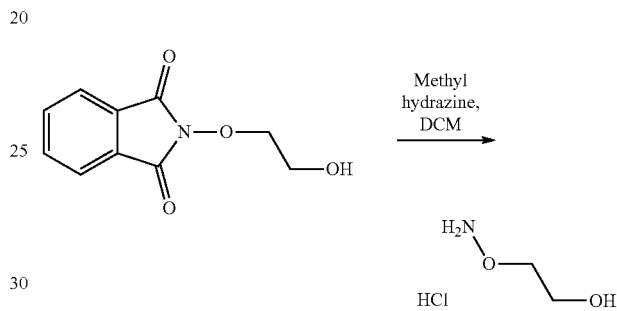

85% methyl hydrazine (1.25 g) was added drop wise to a stirred suspension of 2-(2-hydroxyethoxy)-1H-isoindole-1,3(2H)-dione (6.0 g) in dichloromethane (25 ml) at room temperature and was stirred for 2 hours. Then, the reaction mixture was filtered off under reduced pressure to remove insoluble by-product. The filtrate was concentrated under reduced pressure at lower temperature. The residue was suspended in 2N HCl in Ethylacetate (20 ml) and concentrated under reduced pressure at lower temperature. The resulting solid was triturated with Dichloromethane (2×15 ml) and dried under reduced pressure to give 2.8 g of 2-(aminooxy)ethanol hydrochloride (Yield: 85.5% as mono hydrochloride salt). $^1$H-NMR (DMSO-d6): δ (ppm) 3.61 (m, 2H), 4.04 (t, 2H), 4.73 (m, 1H), 11.02 (s broad, 2H).

N'-(2-hydroxyethoxy)hydrazinecarboximidamide (I-15)

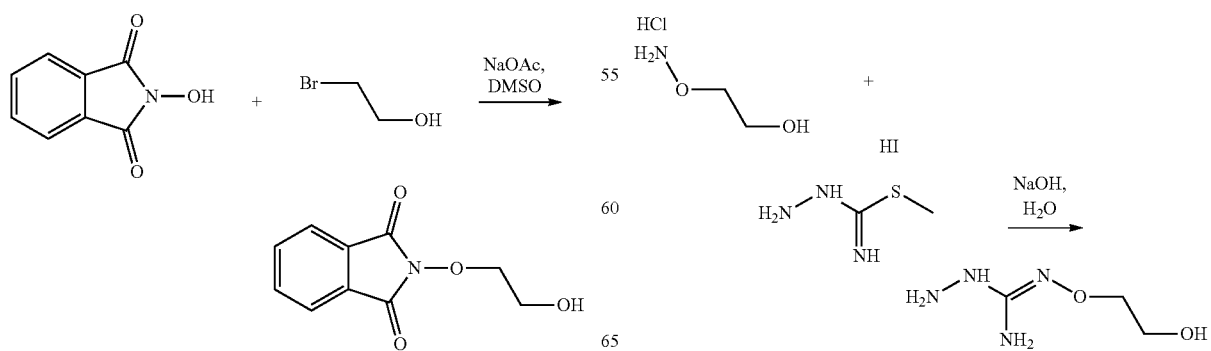

2N NaOH solution (10.6 ml) was added drop wise to a stirred solution of 2-(aminooxy)ethanol hydrochloride salt (2.4 g) and s-methyl isothiosemicarbazide hydroiodide (4.98 g) in water (8.4 ml) at room temperature and was stirred for 24 hours. Formation of N'-(2-hydroxyethoxy)hydrazine carboximidamide was confirmed by LCMS analysis. The mixtures was concentrated under reduced pressure and the resulting residue was azeotroped with methanol (15 ml). The resulting material was suspended in ethanol (10 ml) and the insoluble inorganic salts were removed by filtration. The filtrate containing N'-(2-hydroxyethoxy)hydrazinecarboximidamide was directly used for the next step without any further processing. LC-MS: m/z=134.6 (M+H)

2-(2-chlorobenzylidene)-N'-(2-hydroxyethoxy)hydrazinecarboximidamide (Compound 16)

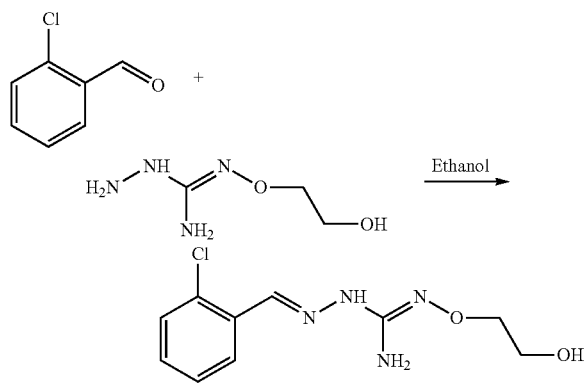

2-chlorobenzaldehyde (3.28 g) was added drop wise to the filtrate containing N'-(2-hydroxyethoxy)hydrazinecarboximidamide at room temperature and was stirred for 2 hours. The reaction mixture was concentrated under reduced pressure and the residue thus obtained was further purified by Prep HPLC using 0.1% $NH_3$/water/MeCN to give 0.24 g of 2-(2-chlorobenzylidene)-N'-(2-hydroxyethoxy)hydrazinecarboximidamide (Yield: 4.4% for 2 steps). $^1$H-NMR (DMSO-d6): δ (ppm) 3.58 (m, 2H), 3.73 (m, 2H), 4.61 (m, 1H), 5.91 (s broad, 2H), 7.32 (m, 2H), 7.44 (m, 1H), 8.13 (m, 1H) 8.16 (s, 1H), 10.43 (m, 1H). LC-MS: m/z=256.73 (M+H).

Compound 17: 2-(2-chlorobenzylidene)-N'-(2-chloroethoxy) Hydrazine Carboximidamide Hydrochloride

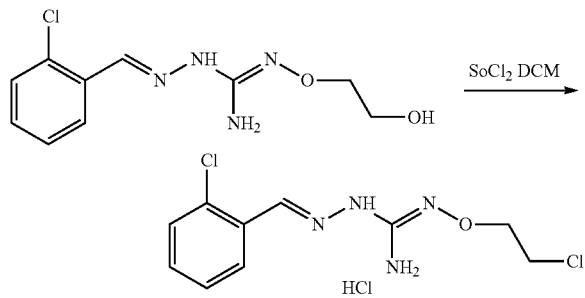

$SoCl_2$ (0.26 ml) was added drop wise to a stirred solution of 2-(2-chlorobenzylidene)-N-(2-hydroxyethoxy)hydrazine carboximidamide (0.22 g) in Dichloromethane (10 ml) at 0° C. The reaction mixture was stirred at the room temperature for 24 hours. Then, the reaction mixtures was concentrated under reduced pressure. The resulting residue was triturated with n-pentane (2×5 ml) and dried under reduced pressure to give 0.26 g of 2-(2-chlorobenzylidene)-N'-(2-chloroethoxy) hydrazinecarboximidamide hydrochloride (Yield: 99.5%). LC-MS: m/z=274.8 (M+H).

Compound 18: 2-(2-chlorobenzylidene)-N'-[2-(pyrrolidin-1-yl) ethoxy]hydrazine Carboximidamide

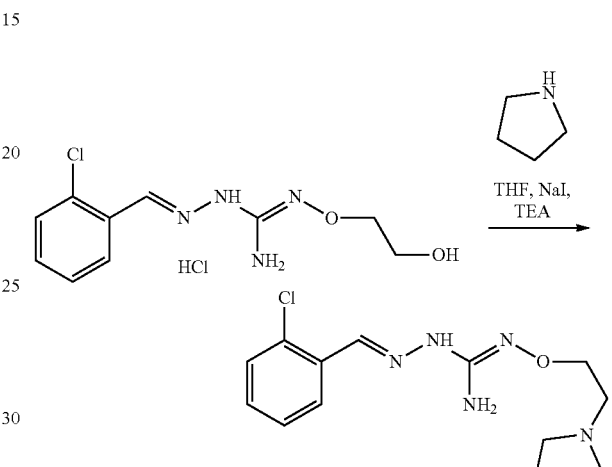

Pyrrolidine (0.23 g) was added to a stirred solution of 2-(2-chlorobenzylidene)-N'-(2-chloroethoxy)hydrazine carboximidamide hydrochloride (0.27 g), Triethylamine (0.35 g) and Sodium iodide (0.04 g) in THF (10 ml) at room temperature. The resulting mixture was stirred at 50° C. for 24 hours. Then, the reaction mixtures was allowed to cool to room temperature and the crude was dumped in 50 ml of cold water. The product was extracted by ethyl acetate (2×50 ml). Then, organic layer were combined and distilled under vacuum, the residue thus obtained was further purified by Prep HPLC using 0.1% $NH_3$/water/MeCN to give 14 mg of 2-(2-chlorobenzylidene)-N'-[2-(pyrrolidin-1-yl)ethoxy]hydrazinecarboximidamide (Yield: 5.3%).). $^1$H-NMR (MeOD): δ (ppm) 1.91 (m, 4H), 2.75 (m, 4H), 2.88 (t, 2H), 3.97 (t, 2H), 7.32 (m, 2H), 7.41 (m, 1H), 8.07 (m, 1H), 8.32 (s, 1H). LC-MS: m/z=310.33 (M+H).

Compound 20: 2-(2-chlorobenzylidene)-N'-ethoxyhydrazinecarboximidamide

N'-(2-ethoxy)hydrazinecarboximidamide (I-16)

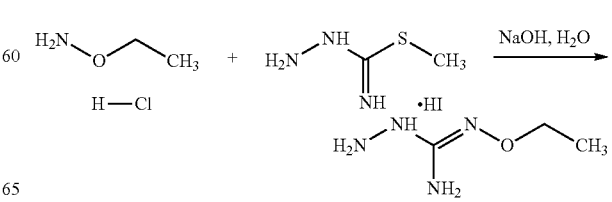

1N NaOH solution (5.12 ml) was added drop wise to a stirred solution of ethoxyamine hydrochloride salt (0.5 g) and s-methyl isothiosemicarbazide hydroiodide (1.19 g) in water (5.0 ml) at room temperature and was stirred for 48 hours. Formation of N'-(2-ethoxy)hydrazinecarboximidamide was confirmed by LCMS analysis. The mixtures was concentrated under reduced pressure and the resulting residue was dissolved in ethanol (15 ml). The insoluble solids were removed by filtration. The filtrate was concentrated and N'-(2-ethoxy)hydrazinecarboximidamide was directly used for the next step without any further processing. LC-MS: m/z=118.8 (M+H).

2-(2-chlorobenzylidene)-N-ethoxyhydrazinecarboximidamide (Compound 20)

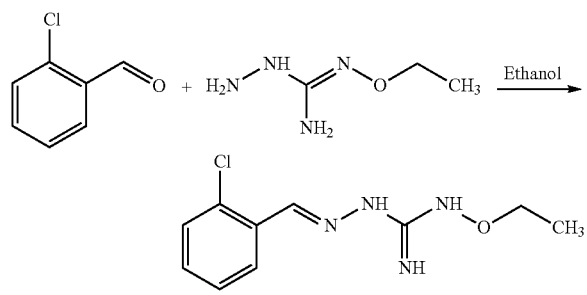

2-chlorobenzaldehyde (0.717 g) was added dropwise to N'-(2-ethoxy)hydrazinecarboximidamide in solution in ethanol (10 ml) and sodium acetate (0.42 g) at room temperature and was stirred for 2 hours at 90° C. The reaction mixture was concentrated under reduced pressure and the residue thus obtained was further purified by chromatography to give 21.4 mg of 2-(2-chlorobenzylidene)-N'-(2-ethoxy)hydrazinecarboximidamide (Yield: 1.7% for 2 steps). $^1$H-NMR (DMSO-d6): δ (ppm) 1.18 (t, 3H), 3.77 (q, 2H), 5.77 (s broad, 2H), 7.31 (m, 2H), 7.43 (m, 1H), 8.11 (m, 1H), 8.15 (s, 1H), 10.45 (s broad, 1H). LC-MS: m/z=240.9 (M+H).

Compound 21: 2-(2,6-dichlorobenzylidene)-N-ethoxyhydrazinecarboximidamide

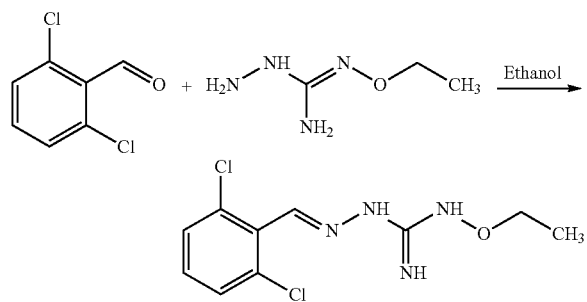

2,6-dichlorobenzaldehyde (0.896 g) was added dropwise to 1 equivalent of N'-(2-ethoxy)hydrazinecarboximidamide (I-16) in solution in ethanol (10 ml) and sodium acetate (0.42 g) at room temperature and was stirred for 2 hours at 90° C. The reaction mixture was concentrated under reduced pressure and the residue thus obtained was further purified by chromatography to give 57 mg of 2-(2,6-dichloroben-zylidene)-N'-(2-ethoxy)hydrazinecarboximidamide (Yield: 4.1% for 2 steps). $^1$H-NMR (DMSO-d6): δ (ppm) 1.77 (t, 3H), 3.78 (q, 2H), 5.48 (s broad, 2H), 7.33 (t, 1H), 7.52 (m, 2H), 8.04 (s, 1H), 8.16 (m, 1H). LC-MS: m/z=277.1 (M+H).

Compound 22: 2-(2-chlorobenzylidene)-N-propoxyhydrazinecarboximidamide N-propoxyhydrazinecarboximidamide (I-17)

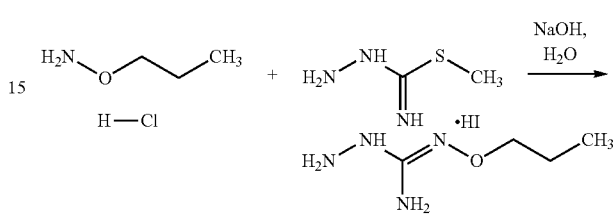

2N NaOH solution (1.23 ml) was added dropwise to a stirred solution of O-propylhydroxylamine hydrochloride salt (0.28 g) and s-methyl isothiosemicarbazide hydroiodide (0.58 g) in water (2.0 ml) at room temperature and was stirred for 24 hours. Formation of N'-(propoxy)hydrazinecarboximidamide was confirmed by LCMS analysis. The mixtures was concentrated under reduced pressure and the resulting residue was dissolved in ethanol (15 ml). The insoluble solids were removed by filtration. The filtrate was concentrated and N'-(propoxy)hydrazinecarboximidamide was directly used for the next step without any further processing. LC-MS: m/z=132.9 (M+H)

2-(2-chlorobenzylidene)-N-propoxyhydrazinecarboximidamide (Compound 22)

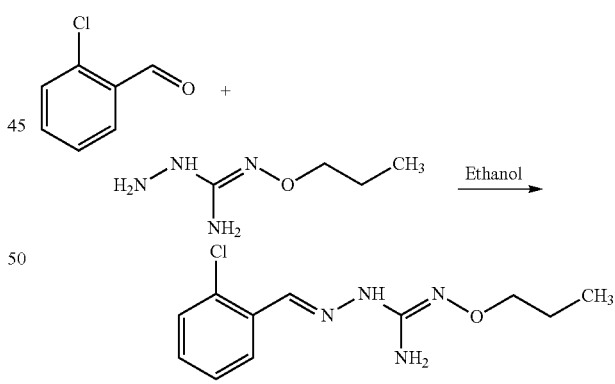

2-chlorobenzaldehyde (0.35 g) was added dropwise to N'-(2-propoxy)hydrazinecarboximidamide in solution in ethanol (10 ml) and was stirred for 2 at room temperature. The reaction mixture was concentrated under reduced pressure and the residue thus obtained was further purified by chromatography to give 25 mg of 2-(2-chlorobenzylidene)-N'-(2-propoxy)hydrazinecarboximidamide (Yield: 3.9% for 2 steps). $^1$H-NMR (DMSO-d6): δ (ppm) 0.88 (t, 3H), 1.58 (m, 2H), 3.66 (t, 2H), 5.75 (s broad, 2H), 7.29 (m, 2H), 7.41 (m, 1H), 8.10 (m, 2H), 10.45 (s broad, 2H). LC-MS: m/z=255.1 (M+H).

Compound 23: 2-(2-chlorobenzylidene)-N-(2-ethoxyethoxy) Hydrazinecarboximidamide

2-(2-ethoxyethoxy)-1,3-dimethylidene-2,3-dihydro-1H-isoindole (I-18)

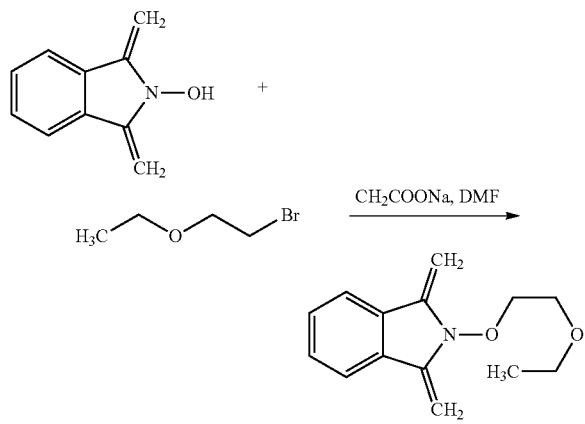

The N-hydroxypthalimide (4.0 g) and 1-bromo-2-ethoxyethane (11.25 g) were dissolved in DMF (40.0 ml) and CH$_3$COONa (10.0 g) was added to the solution at room temperature. The reaction mixture was allowed to stir at 70° C. for 12 hours. The reaction mixture was allowed to cool to room temperature and was and was poured in water and then extracted two times by ethyl acetate. The organic layer was concentrated under reduce pressure and was purified by column chromatography using silica gel. The desired product was eluted with 0-30% ethyl acetate in hexane. Evaporation of pure product fractions gave 4.8 g of 2-(2-ethoxyethoxy)-1,3-dimethylidene-2,3-dihydro-1H-isoindole (I-18) (Yield: 83.3%). $^1$H-NMR (DMSO-d6): δ (ppm) 0.98 (t, 3H), 3.39 (q, 2H), 3.73 (t, 2H), 4.27 (t, 2H), 7.87 (s, 4H). LC-MS: m/z=236.2 (M+H).

1-(aminooxy)-2-ethoxyethane Hydrochloride (I-19)

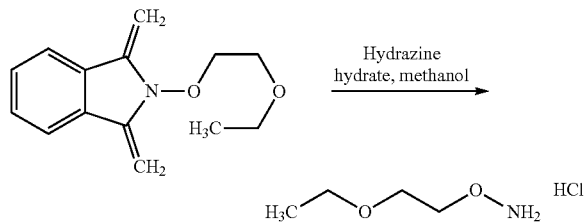

Hydrazine hydrate (1.32 g) was added dropwise to a stirred solution of 2-(2-ethoxyethoxy)-1,3-dimethylidene-2,3-dihydro-1H-isoindole (4.8 g) in methanol (10 ml) at room temperature and was stirred for 30 minutes. Then, the reaction mixture was filtered off under reduced pressure to remove insoluble by-product. The filtrate was concentrated under reduced pressure at lower temperature and triturated ether and insoluble was removed by filtration. Then, to the filtrate, 4N HCl in dioxane (10.2 ml) was added dropwise and the precipitated salt was collected by filtration and was dried to 2.0 g of 1-(aminooxy)-2-ethoxyethane hydrochloride (Yield: 69.4% as mono hydrochloride salt). $^1$H-NMR (DMSO-d6): δ (ppm) 1.11 (t, 3H), 3.44 (q, 2H), 3.59 (m, 2H), 4.14 (m, 2H), 11.02 (s broad, 2H). LC-MS: m/z=106.1 (M+H).

N'-(2-ethoxyethoxy)hydrazinecarboximidamide (I-20)

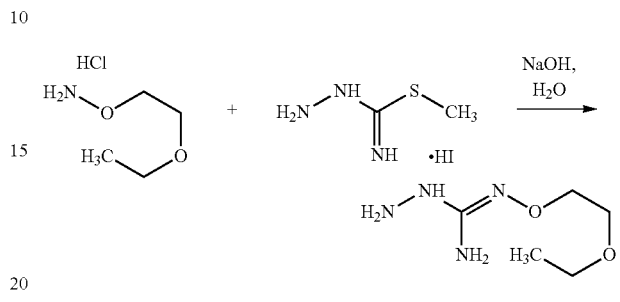

1N NaOH solution (4.23 ml) was added dropwise to a stirred solution of 1-(aminooxy)-2-ethoxyethane hydrochloride salt (0.6 g) and s-methyl isothiosemicarbazide hydroiodide (0.99 g) in water (2.1 ml) at room temperature and was stirred for 48 hours. Formation of N'-(2-ethoxyethoxy)hydrazinecarboximidamide was confirmed by LCMS analysis. The mixtures was concentrated under reduced pressure and the resulting residue was dissolved in ethanol (10 ml). The insoluble solids were removed by filtration. The filtrate was concentrated and N'-(2-ethoxyethoxy)hydrazinecarboximidamide was directly used for the next step without any further processing. LC-MS: m/z=163.0 (M+H).

2-(2-chlorobenzylidene)-N-(2-ethoxyethoxy)hydrazinecarboximidamide (Compound 23)

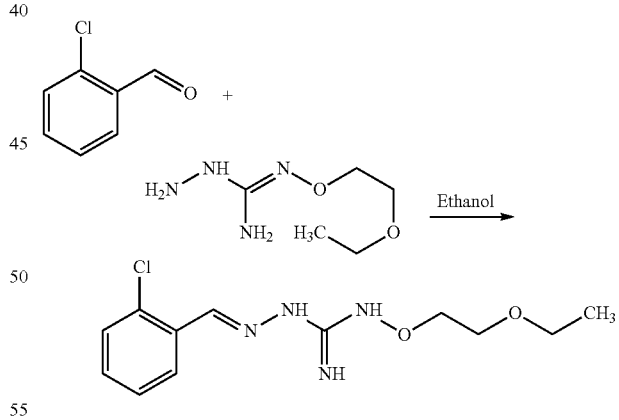

2-chlorobenzaldehyde (0.59 g) was added dropwise to N'-(2-ethoxyethoxy) hydrazinecarboximidamide in solution in ethanol (5 ml) and was stirred for 2 at room temperature. The reaction mixture was concentrated under reduced pressure and the residue thus obtained was further purified by chromatography to give 19 mg of 2-(2-chlorobenzylidene)-N'-(2-propoxy)hydrazinecarboximidamide (Yield: 1.8% for 2 steps). $^1$H-NMR (DMSO-d6): δ (ppm) 1.24 (t, 3H), 3.48 (q, 2H), 3.56 (m, 2H), 3.83 (m, 2H), 5.80 (s broad, 2H), 7.43 (m, 1H), 8.12 (m, 1H), 8.17 (s, 1H), 10.50 (s broad, 2H). LC-MS: m/z=285.0 (M+H).

Compound 24: 2-(2-chlorobenzylidene)-N'-[(3-methylbut-2-en-1-yl)oxy]hydrazinecarboximidamide 2-[(3-methylbut-2-en-1-yl)oxy]-1H-isoindole-1,3(2H)-dione (I-21)

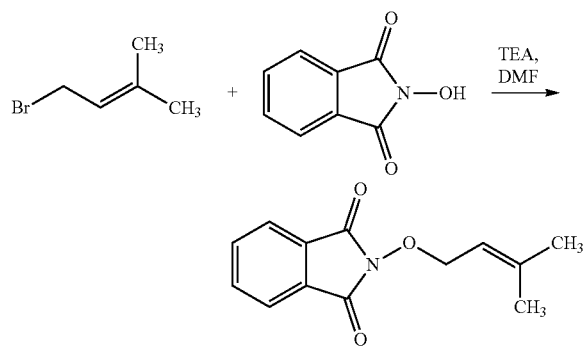

Triethylamine (12.13 g) was added dropwise to a stirred solution of N-Hydroxyphthalimide (9.85 g) and 1-bromo-3-methyl butene (9.0 g) in DMF (30 ml) at room temperature. The reaction mixture was stirred at 70° C. for 2 hours. The reaction mixture was allowed to cool to room temperature. The mixture was concentrated under reduced pressure and the residue thus obtained was suspended in cold water. The resulting suspension was stirred well for some time and the solid was filtered off under reduced pressure. The solid was further washed with demineralized water (200 ml) and hexane (100 ml). The resulting solid was dried under reduced pressure to get a crude material which was purified by column chromatography using silica gel to give 9.0 g of –[(3-methylbut-2-en-1-yl)oxy]-1H-isoindole-1,3(2H)-dione (Yield: 64.5%). $^1$H-NMR (DMSO-d6): δ (ppm) 1.70 (d, 6H), 4.63 (m, 2H), 5.45 (m, 1H), 7.87 (s, 4H). LC-MS: m/z=232.1 (M+H).

1-(aminooxy)-3-methylbut-2-ene Hydrochloride (I-22)

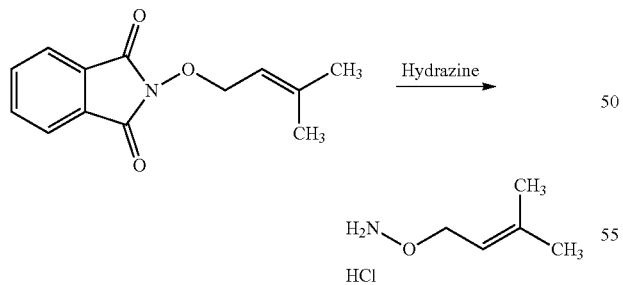

Hydrazine hydrate (2.52 g) was added dropwise to a stirred solution of 2-[(3-methylbut-2-en-1-yl)oxy]-1H-isoindole-1,3(2H)-dione (9.0 g) in methanol (120 ml) at room temperature. The reaction mixture was stirred at the same temperature for 30 min. The reaction mixture was filtered off to remove the insoluble by-product and the resulting filtrate was concentrated under reduced pressure to get a crude material which was purified by column chromatography using silica gel. The crude was triturated with ether and insoluble mass was removed by filtration. The filtrate was treated with 4 M HCl in dioxane (19 ml) dropwise and the precipitate was filtered, collected and dried under vacuum to give 2.9 g of 1-(aminooxy)-3-methylbut-2-ene hydrochloride (Yield: 73.6%). $^1$H-NMR (DMSO-d6): δ (ppm) 1.70 (s, 3H), 1.75 (s, 3H), 1.65 (m, 1H), 4.50 (d, 2H), 5.30 (t, 1H), 10.89 (s, 3H).

N'-[(3-methylbut-2-en-1-yl)oxy]hydrazinecarboximidamide (I-23)

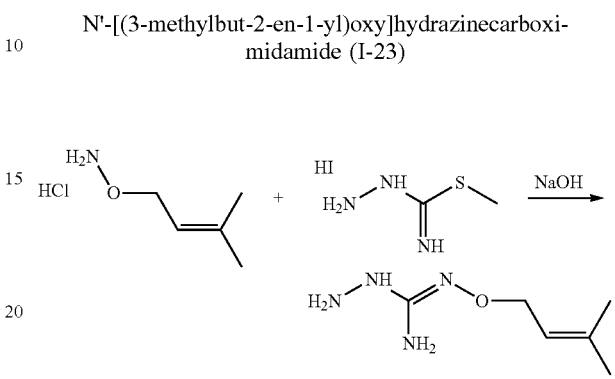

1N NaOH solution (3.63 ml) was added dropwise to a stirred solution of 1-(aminooxy)-3-methylbut-2-ene hydrochloride (0.5 g) and s-methylisothiosemicarbazide hydroiodide (0.85 g) in water (3 ml) at room temperature and was stirred for 48 hours. Then, the reaction mixtures was concentrated under reduced pressure. The resulting residue was suspended in ethanol (15 ml) and insoluble inorganic salts were removed by filtration. The filtrate was concentrated and directly used for the next step without any further processing. N'-[(3-methylbut-2-en-1-yl)oxy] hydrazinecarboximidamide was confirmed by LCMS analysis. LC-MS: m/z=159.15 (M+H).

2-(2-chlorobenzylidene)-N'-[(3-methylbut-2-en-1-yl)oxy]hydrazinecarboximidamide (Compound 24)

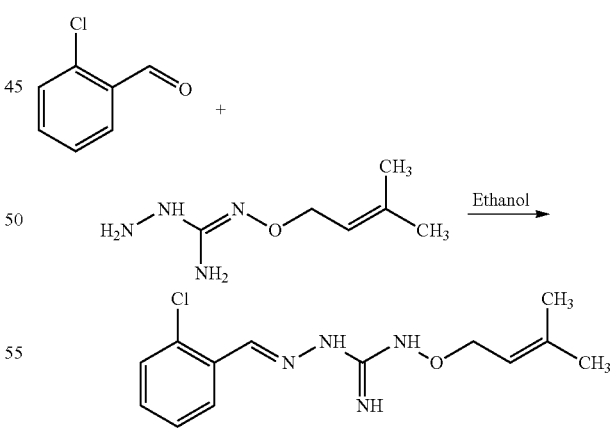

2-chlorobenzaldehyde (0.5 g) was added dropwise to N'-[(3-methylbut-2-en-1-yl)oxy]hydrazinecarboximidamide in solution in ethanol (3 ml) at room temperature and was stirred for 2 hours at 90° C. The reaction mixture was concentrated under reduced pressure and the residue thus obtained was further purified by chromatography to give 139 mg of 2-(2-chlorobenzylidene)-N'-[(3-methylbut-2-en-1-yl)oxy]hydrazinecarboximidamide (Yield: 13.5% for 2 steps).

¹H-NMR (DMSO-d6): δ (ppm) 1.64 (s, 3H), 1.71 (s, 3H), 3.17 (s, 1H), 4.25 (d, 2H), 5.39 (t, 1H), 5.75 (s broad, 2H), 7.32 (m, 1H), 7.43 (m, 1H), 8.10 (m, 1H), 8.15 (m, 1H), 8.17 (s broad, 1H). LC-MS: m/z=281.2 (M+H).

Compound 25: 2-(2-chlorobenzylidene)-N-[2-(ethylsulfanyl) Ethoxy]hydrazinecarboximidamide 2-bromoethyl Ethyl Sulphide (I-24)

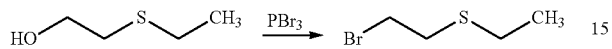

PBr₃ (10 ml) was added dropwise to 2-(ethylsulfanyl) ethanol in solution in dichloromethane (100 ml) at 0° C. and was stirred for 2 hours. Then the reaction mixture was warmed to room temperature and stirred for 16 hours. The reaction mixture was cooled at 0° C. and 10 ml of water was added. Then reaction mixture was neutralized with saturated Na₂CO₃ solution (~up to Ph 7) and extracted with dichloromethane (3×250 ml). The organic layers were separated, combined and dried (Na₂SO₄) and concentrated to afford 13.0 g of 2-bromoethyl ethyl sulphide (yield: 72.7%). ¹H-NMR (CDCl₃): δ (ppm) 1.30 (t, 3H), 2.62 (q, 2H), 2.97 (m, 2H), 3.50 (m, 2H).

2-[2-(ethylsulfanyl)ethoxy]-1H-isoindole-1,3(2H)-dione (I-25)

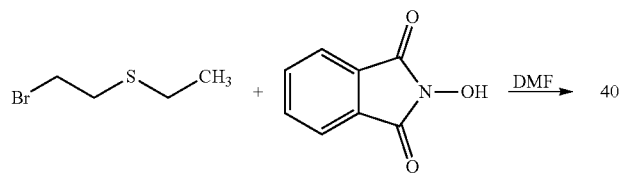

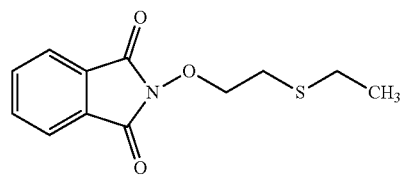

The N-hydroxypthalimide (3.9 g) and 2-bromoethyl ethyl sulphide (12.1 g) were dissolved in DMF (40.0 ml) and CH₃COONa (9.7 g) was added portionwise to the solution at room temperature. The reaction mixture was allowed to stir at 70° C. for 2 hours. The reaction mixture was allowed to cool to room temperature and was and was poured in cold water and then extracted two times by ethyl acetate. The organic layer was concentrated under reduce pressure and was purified by column chromatography using silica gel. To give 6.0 g of 2-[2-(ethylsulfanyl)ethoxy]-1H-isoindole-1,3 (2H)-dione (I-25) (Yield: 98%). ¹H-NMR (CDCl₃): δ (ppm) 1.29 (t, 3H), 2.63 (q, 2H), 2.94 (t, 2H), 4.36 (t, 2H), 7.77 (m, 2H), 7.86 (m, 2H).

1-(aminooxy)-2-(ethylsulfanyl)ethane Hydrochloride (I-26)

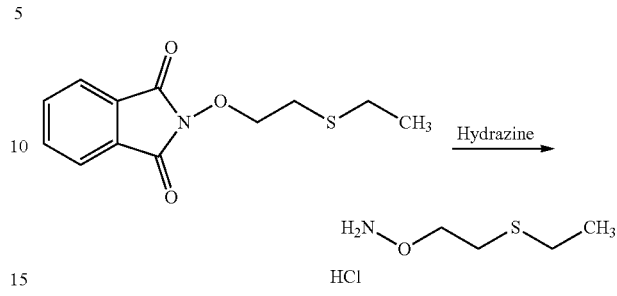

Hydrazine hydrate (0.25 g) was added dropwise to a stirred solution of 2-[2-(ethylsulfanyl)ethoxy]-1H-isoindole-1,3(2H)-dione (1.0 g) in methanol (10 ml) at room temperature. The reaction mixture was stirred at the same temperature for 30 min. The reaction mixture was filtered off to remove the insoluble by-product and the resulting filtrate was concentrated under reduced pressure then dissolved in DCM and insoluble removed by filtration. The filtrate was concentrated under reduced pressure then, the crude was triturated with ether and insoluble mass was removed by filtration. The filtrate was treated with 4 M HCl in dioxane (2 ml) dropwise. Then the solvent was removed by evaporation and the the residue was triturated with diethyl ether to provide 454 mg 1-(aminooxy)-2-(ethylsulfanyl)ethane hydrochloride (Yield: 72.5%). ¹H-NMR (DMSO-d6): δ (ppm) 1.18 (s, 3H), 2.53 (m, 2H), 2.79 (t, 2H), 4.16 (t, 2H), 11.14 (s broad, 3H).

N'-[2-(ethylsulfanyl)ethoxy]hydrazinecarboximidamide (I-27)

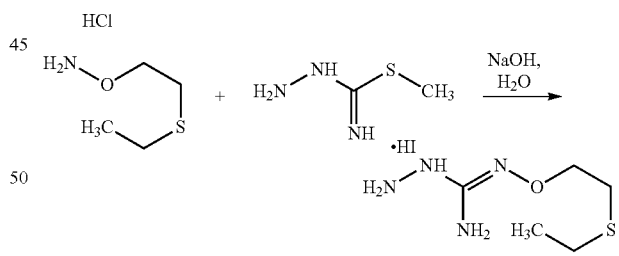

1N NaOH solution (2.88 ml) was added dropwise to a stirred solution of 1-(aminooxy)-2-(ethylsulfanyl)ethane hydrochloride (0.5 g) and s-methyl isothiosemicarbazide hydroiodide (0.7 g) in water (5 ml) at room temperature and was stirred for 48 hours. The mixtures was concentrated under reduced pressure and the resulting residue was dissolved in ethanol (15 ml). The insoluble solids were removed by filtration. The filtrate was concentrated and N'-[2-(ethylsulfanyl)ethoxy]hydrazinecarboximidamide was directly used for the next step without any further processing.

2-(2-chlorobenzylidene)-N-[2-(ethylsulfanyl)ethoxy]hydrazinecarboximidamide (Compound 25)

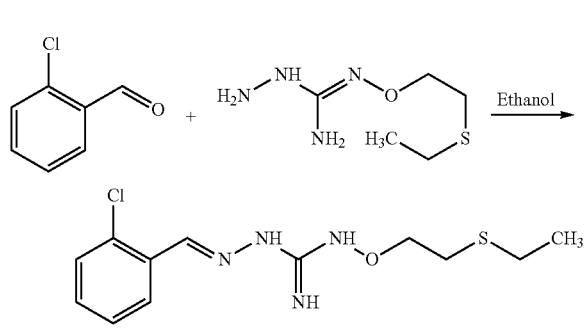

2-chlorobenzaldehyde (0.4 g) was added dropwise to N'-[2-(ethylsulfanyl)ethoxy]hydrazinecarboximidamide in solution in ethanol (5 ml) and was stirred for 2 at room temperature. The reaction mixture was concentrated under reduced pressure and the residue thus obtained was further purified by chromatography to give 15 mg of 2-(2-chlorobenzylidene)-N-[2-(ethylsulfanyl)ethoxy]hydrazinecarboximidamide (Yield: 1.5% for 2 steps). $^1$H-NMR (DMSO-d6): δ (ppm) 1.90 (t, 3H), 2.54 (q, 2H), 2.75 (t, 2H), 3.85 (t, 2H), 5.84 (s broad, 2H), 7.30 (m, 2H), 7.44 (m, 1H), 8.12 (m, 1H), 8.16 (s, 1H), 10.50 (s broad, 1H). LC-MS: m/z=301.9 (M+H).

Compound 26: 2-[(3-chloropyridin-4-yl)methylidene]-N-ethoxyhydrazinecarboximidamide

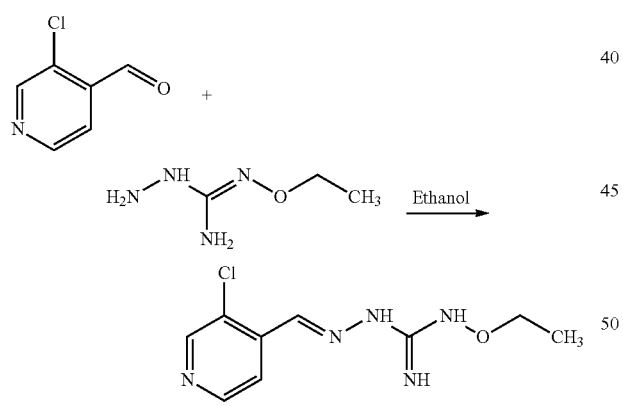

3-chloroisonicotinaldehyde (0.72 g) was added dropwise to 1 equivalent of N'-(2-ethoxy)hydrazinecarboximidamide (I-16) in solution in ethanol (5 ml) and sodium acetate (0.42 g) at room temperature and was stirred for 2 hours at 80° C. The reaction mixture was concentrated under reduced pressure and the residue thus obtained was further purified by chromatography to give 184 mg of 2-[(3-chloropyridin-4-yl)methylidene]-N-ethoxyhydrazinecarboximidamide (Yield: 15% for 2 steps). $^1$H-NMR (DMSO-d6): δ (ppm) 1.19 (t, 3H), 3.79 (q, 2H), 5.96 (s broad, 2H), 8.05 (s, 1H), 8.11 (d, 1H), 8.41 (s, 1H), 10.89 (s broad, 1H). LC-MS: m/z=242.0 (M+H).

Compound 27: 2-(2-chloro-6-fluorobenzylidene)-N-ethoxyhydrazinecarboximidamide

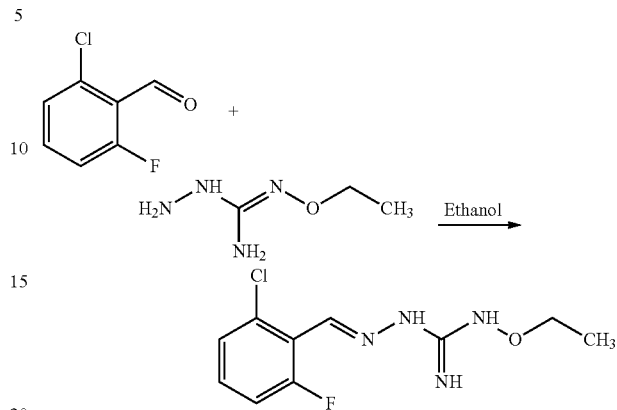

2-chloro-6-flurobenzaldehyde (0.81 g) was added dropwise to 1 equivalent of N'-(2-ethoxy)hydrazinecarboximidamide (I-16) in solution in ethanol (5 ml) and sodium acetate (0.42 g) at room temperature and was stirred for 2 hours at 80° C. The reaction mixture was concentrated under reduced pressure and the residue thus obtained was further purified by chromatography to give 215 mg of 2-(2-chloro-6-fluorobenzylidene)-N-ethoxyhydrazinecarboximidamide (Yield: 17.2% for 2 steps). $^1$H-NMR (DMSO-d6): δ (ppm) 1.17 (m, 3H), 3.78 (q, 2H), 5.48 (s broad, 2H), 7.30 (m, 3H), 8.01 (s, 1H), 10.54 (s broad, 1H). LC-MS: m/z=258.9 (M+H).

Compound 28: N'-butoxy-2-(2-chlorobenzylidene)hydrazinecarboximidamide

N'-butoxoxyhydrazinecarboximidamide (I-28)

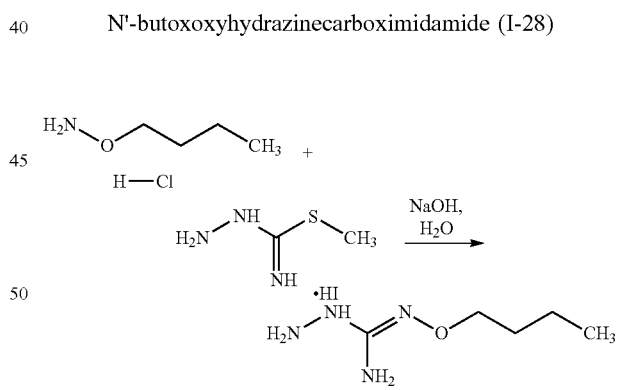

2N NaOH solution (4.0 ml) was added dropwise to a stirred solution of O-butylhydroxylamine hydrochloride salt (1 g) and s-methyl isothiosemicarbazide hydroiodide (1.86 g) in water (5.0 ml) at room temperature and was stirred for 24 hours. Formation of N'-(butoxy)hydrazinecarboximidamide was confirmed by LCMS analysis. The mixtures was concentrated under reduced pressure and the resulting residue was dissolved in ethanol (30 ml). The insoluble solids were removed by filtration. The filtrate was concentrated and N'-(propoxy)hydrazinecarboximidamide was directly used for the next step without any further processing. LC-MS: m/z=146.9 (M+H)

N'-butoxy-2-(2-chlorobenzylidene)hydrazinecarboximidamide (Compound 28)

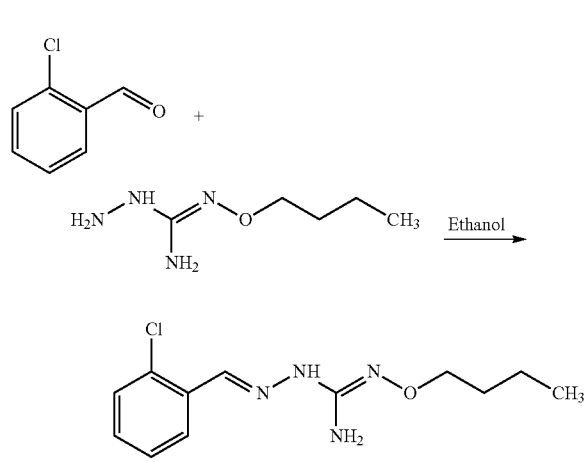

Compound 28 is prepared following the same procedure than compound 22 from 2-chlorobenzaldehyde (1.13 g) and N'-(2-butoxy)hydrazinecarboximidamide (I-28) to give 202 mg of N'-butoxy-2-(2-chlorobenzylidene)hydrazinecarboximidamide (Yield: 8% for 2 steps). $^1$H-NMR (DMSO-d6): δ (ppm) 0.91 (q, 3H), 1.35 (m, 2H), 1.57 (m, 2H), 3.73 (t, 2H), 5.22 and 5.74 (2 s, 2H), 7.30 (m, 2H), 7.43 (m, 1H), 8.11 and 8.53 (m and s, 2H), 10.30 and 10.45 (s and s broad, 1H). LC-MS: m/z=269.0 (M+H).

Compound 29: 2-(2-chloro-6-fluorobenzylidene)-N'-propoxyhydrazinecarboximidamide Compound 19 is prepared following the same procedure than compound 17 from 2-chloro-6-flurobenzaldehyde (1.89 g) and N'-(2-propoxy)hydrazine carboximidamide (I-17) to give 192 mg of 2-(2-chloro-6-fluorobenzylidene)-N-propoxyhydrazinecarboximidamide (Yield: 5.1% for 2 steps). $^1$H-NMR (DMSO-d6): δ (ppm) 0.90 (t, 3H), 1.59 (m, 2H), 3.69 (m, 2H), 4.97 and 5.47 (2s, 1H), 7.25 (m, 1H), 7.31 (m, 1H), 8.01 and 8.40 (2s, 1H), 10.43 and 10.55 (s and s broad, 1H). LC-MS: m/z=273.0 (M+H).

Compound 30: 2-(2-chloro-6-fluorobenzylidene)-N'-butoxyhydrazinecarboximidamide

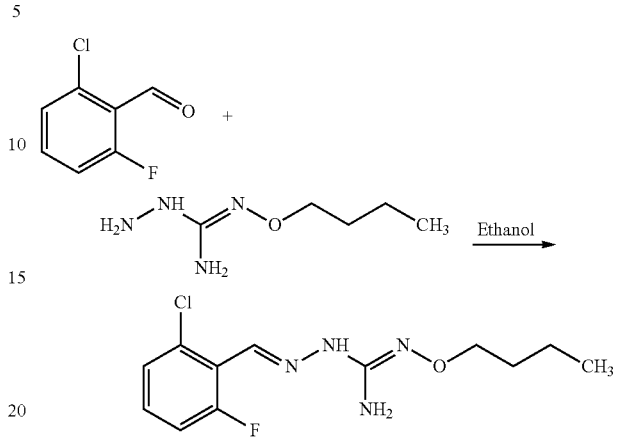

Compound 30 is prepared following the same procedure than compound 29 from 2-chloro-6-flurobenzaldehyde (1.26 g) and N'-(2-butoxy)hydrazinecarboximidamide (I-28) to give 125 mg of N'-butoxy-2-(2-chlorobenzylidene)hydrazinecarboximidamide (Yield: 4.8% for 2 steps). $^1$H-NMR (DMSO-d6): δ (ppm) 0.90 (t, 3H), 1.35 (m, 2H), 1.57 (m, 2H), 3.72 (m, 2H), 7.26 (m, 1H), 7.35 (m, 2H), 8.10 and 8.40 (2s, 1H), 10.41 and 10.56 (s and s broad, 1H). LC-MS: m/z=287.0 (M+H).

Compound 31: 2-(2,6-dichlorobenzylidene)-N-propoxyhydrazinecarboximidamide

Compound 31 is prepared following the same procedure than compound 17 from 2,6-dichlorobenzaldehyde (1.56 g) and N'-(2-propoxy)hydrazine carboximidamide (I-17) to give 127 mg of 2-(2-chloro-6-fluorobenzylidene)-N'-propoxyhydrazinecarboximidamide (Yield: 4.9% for 2 steps). $^1$H-NMR (DMSO-d6): δ (ppm) 0.90 (t, 3H), 1.59 (m, 2H), 3.69 (m, 2H), 4.96 and 5.46 (2s broad, 2H), 7.34 (m, 1H), 7.51 (m, 2H), 8.03 and 8.41 (2s, 1H), 10.43 and 10.52 (2s broad, 1H). LC-MS: m/z=290.9 (M+H).

Compound 32: 2-(2,6-dichlorobenzylidene)-N-butoxyhydrazinecarboximidamide

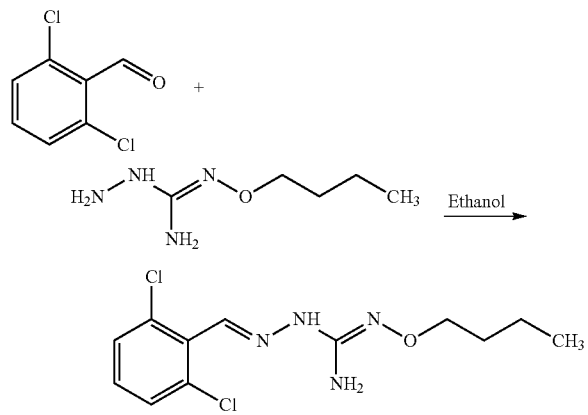

Compound 32 is prepared following the same procedure than compound 22 from 2,6-dichlorobenzaldehyde (1.38 g) and N'-(2-butoxy)hydrazinecarboximidamide (I-28) to give 202 mg of N'-butoxy-2-(2-chlorobenzylidene)hydrazinecarboximidamide (Yield: 8.4% for 2 steps). $^1$H-NMR (DMSO-d6): δ (ppm) 0.92 (m, 3H), 1.35 (m, 2H), 1.58 (m, 2H), 3.72 (m, 2H), 4.95 and 5.41 (2s, 2H), 7.34 (m, 1H), 7.51 (m, 2H), 8.03 and 8.41 (2s, 1H), 10.42 and 10.52 (2s broad, 1H). LC-MS: m/z=303.0 (M+H).

Compound 33: 2-[(3-chloropyridin-4-yl)methylidene]-N-propoxyhydrazinecarboximidamide

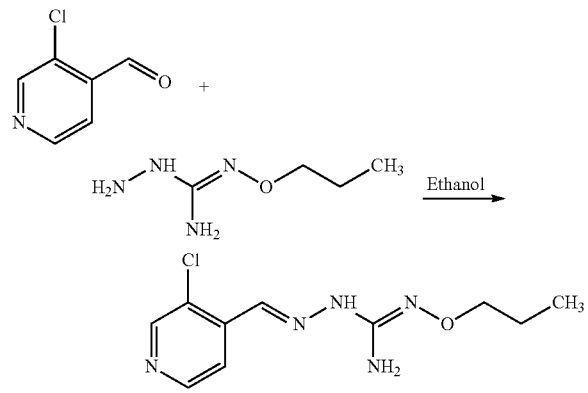

Compound 33 is prepared following the same procedure than compound 17 from 3-chloroisonicotinaldehyde (1.69 g) and N'-(2-propoxy)hydrazine carboximidamide (I-17) to give 240 mg of give 2-(2-chloro-6-fluorobenzylidene)-N'-propoxyhydrazinecarboximidamide (Yield: 7.9% for 2 steps). $^1$H-NMR (DMSO-d6): δ (ppm) 0.90 (t, 3H), 1.60 (m, 2H), 3.69 (t, 2H), 5.94 (s, 2H), 8.04 (s, 1H), 8.11 (d, 1H), 8.41 (d, 1H), 8.57 (s, 1H), 10.91 s broad, 1H). LC-MS: m/z=255.9 (M+H).

Selected compounds according to the invention are set forth in Table 1 below:

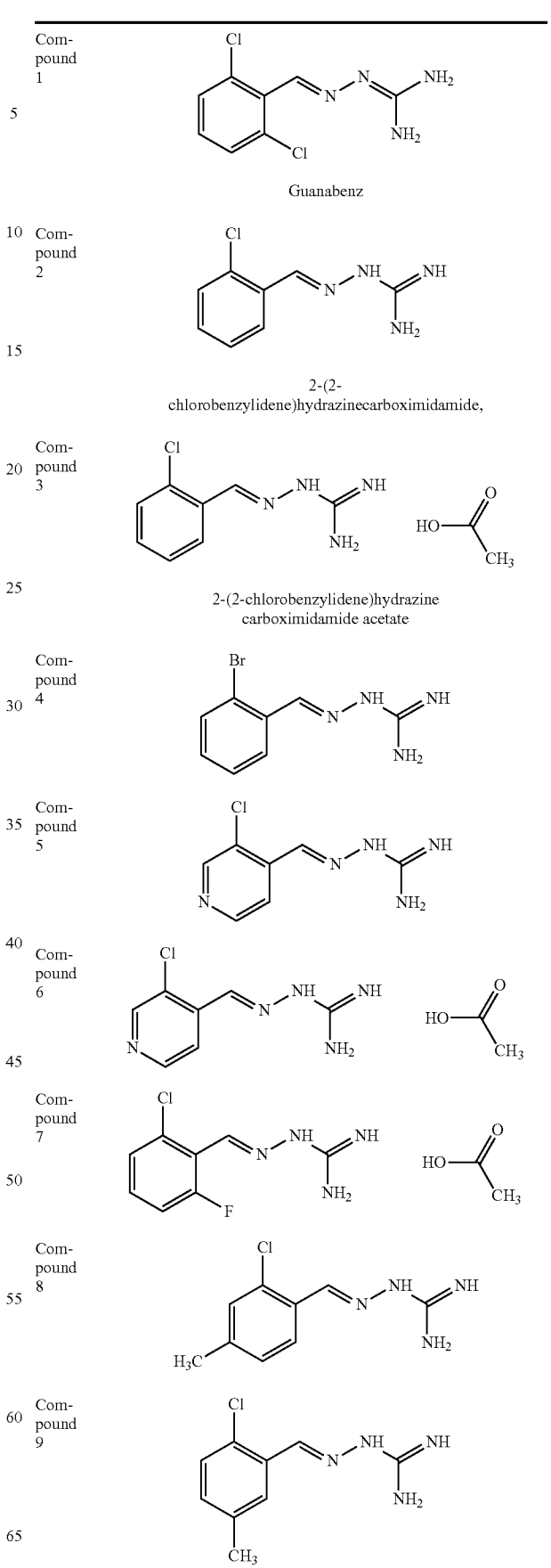

| Compound 1 | Guanabenz |
| Compound 2 | 2-(2-chlorobenzylidene)hydrazinecarboximidamide, |
| Compound 3 | 2-(2-chlorobenzylidene)hydrazine carboximidamide acetate |
| Compound 4 | |
| Compound 5 | |
| Compound 6 | |
| Compound 7 | |
| Compound 8 | |
| Compound 9 | |

| | | | |
|---|---|---|---|
| Compound 10 | 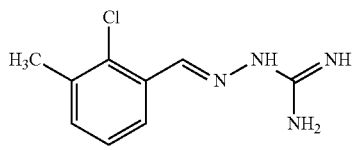 | Compound 19 | 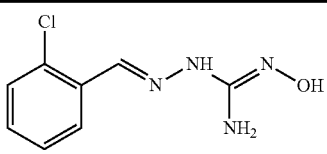 |
| Compound 11 | 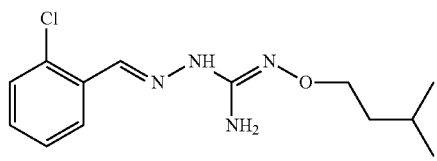 [SMILES: CC(C)CCO/N=C(\N)N/N=C/c1ccccc1Cl]<br>HCOOH | Compound 20 | 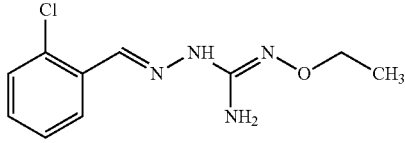<br>2-(2-chlorobenzylidene)-N'-ethoxyhydrazinecarboximidamide |
| Compound 12 | 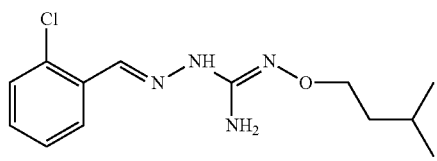 | Compound 21 | 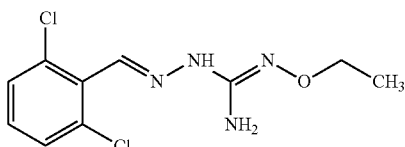 |
| Compound 13 | 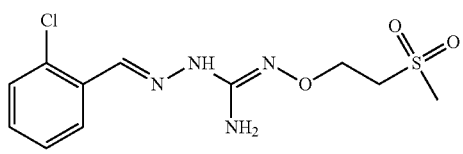 [SMILES: CS(=O)(=O)CCO/N=C(\N)N/N=C/c1ccccc1Cl] | Compound 22 | 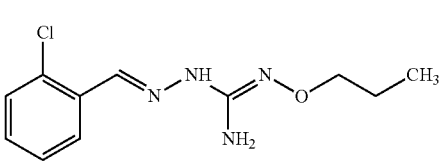<br>2-(2-chlorobenzylidene)-N-propoxyhydrazinecarboximidamide |
| Compound 14 | 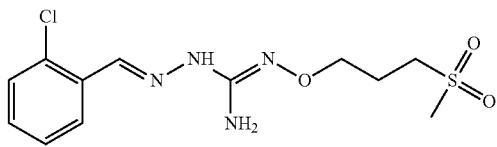 [SMILES: CS(=O)(=O)CCCO/N=C(\N)N/N=C/c1ccccc1Cl] | Compound 23 | 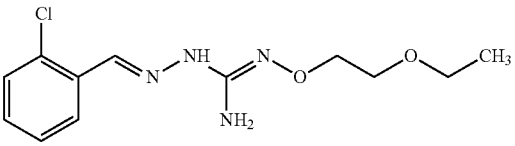 |
| Compound 15 | 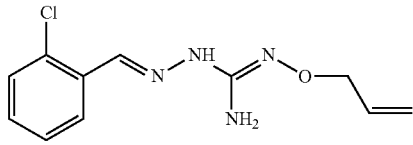 [SMILES: C=CCO/N=C(\N)N/N=C/c1ccccc1Cl] | Compound 24 | 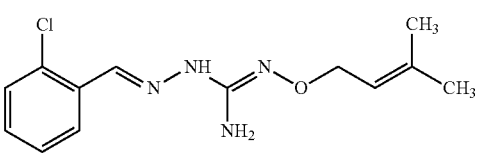 |
| Compound 16 | 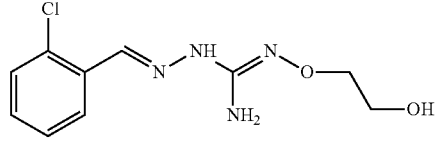 [SMILES: N/C(=N\OCCO)N/N=C/c1ccccc1Cl] | Compound 25 | 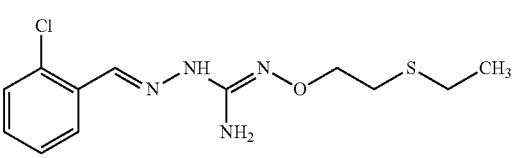 [SMILES: CCOCCO/N=C(\N)N/N=C/c1ccccc1Cl] |
| Compound 17 | 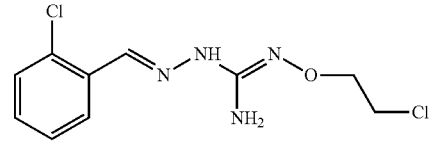<br>HCl | Compound 26 | 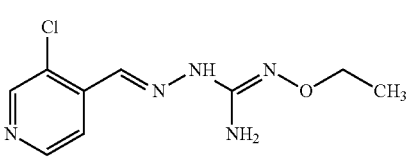 [SMILES: CCO/N=C(\N)N/N=C/c1ccncc1Cl] |
| Compound 18 | 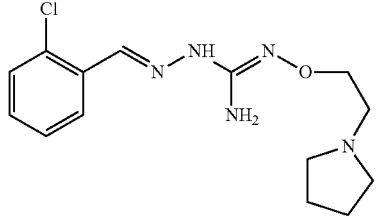 | Compound 27 | 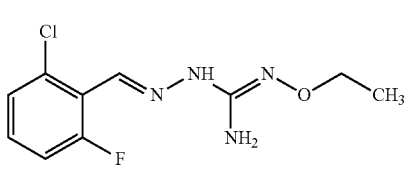 [SMILES: CCO/N=C(\N)N/N=C/c1c(F)cccc1Cl] |

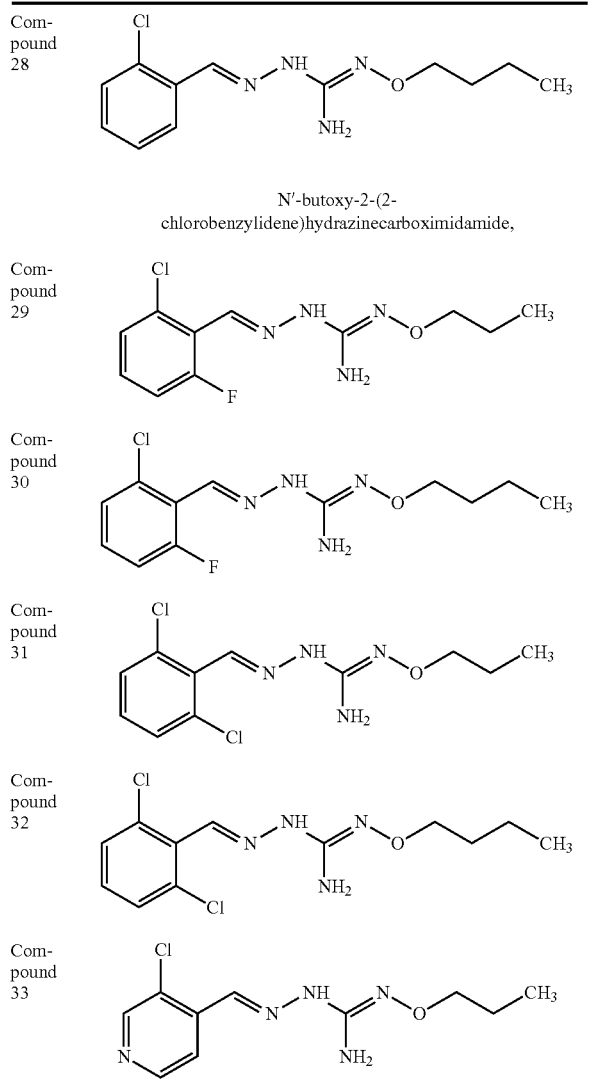

| Compound 28 | N'-butoxy-2-(2-chlorobenzylidene)hydrazinecarboximidamide, |
|---|---|
| Compound 29 | |
| Compound 30 | |
| Compound 31 | |
| Compound 32 | |
| Compound 33 | |

In some of the experiments below, the salt of these compounds may be used; for example, the acetate salt of example 1 formed with acetic acid may be used.

1.2—Embryonated Chicken Eggs

Fertilized White Leghorn eggs were incubated at 38° C. with 60% relative humidity for 9 days. At this time (E9), the chorio-allantoic membrane (CAM) was dropped by drilling a small hole through the eggshell into the air sac and a 1 cm$^2$ window was cut in the eggshell above the CAM.

1.3—Tumor Induction

Cultured glioblastoma cell line GL261 were detached by trypsinization, washed with complete medium, labeled and suspended in serum free DMEM. An inoculum of GL261 cells was added onto the CAM of each egg. Eggs were then randomized in 6 groups.

1.4—Treatments

At day 10 (E10), tumors began to be detectable. They were then treated during 10 days, every two days (E10, E12, E14, E16, E18), by dropping 100 µl of test compound (100 nM), Temozolomide (500 microM), test compound (100 nM) and Temozolomide (500 microM), or Control (0.02% DMSO) onto the tumor.

1.5—Tumor Growth Analysis

At day E19 the upper portion of the CAM was removed, transferred in PBS and the tumors were then carefully cut away from normal CAM tissue. Tumors were then weighted. In parallel, a 1 cm$^2$ portion of the lower CAM was collected to evaluate the number of nodules, containing expressing cells. The fluorescent nodules were visualized in situ using whole mounts of fixed tissue and flattened between a hollow glass slide and a thick coverslip. In order to number the nodules, a thorough and complete visual scan of the piece of the lower CAM was done using fluorescent microscope.

2—Results

Glioblastoma cell line GL261 was grafted on the chorio-allantoic membrane (CAM) of Fertilized White Leghorn eggs. The tumors were treated every two days with test compound (100 mM), temolozomide (500 microM) or test compound (100 nM) and temozolomide (500 microM). For the control, the tumors were treated with 0.02% DMSO. Between seven (7) to eighteen (18) eggs were treated for each condition.

Temozolomide alone (500 microM) is able to reduce the GL261 tumor size as accredited by the decrease tumor weight (mg) compared to control.

Compound 1 (guanabenz) alone (100 nM) has no effect to reduce the tumor size. Together compound 1 (100 nM) and temozolomide (500 microM) have a synergistic effect to reduce the tumor size on the upper CAM compare to temozolomide alone or compound 1 alone (FIG. 1).

Figure 2:
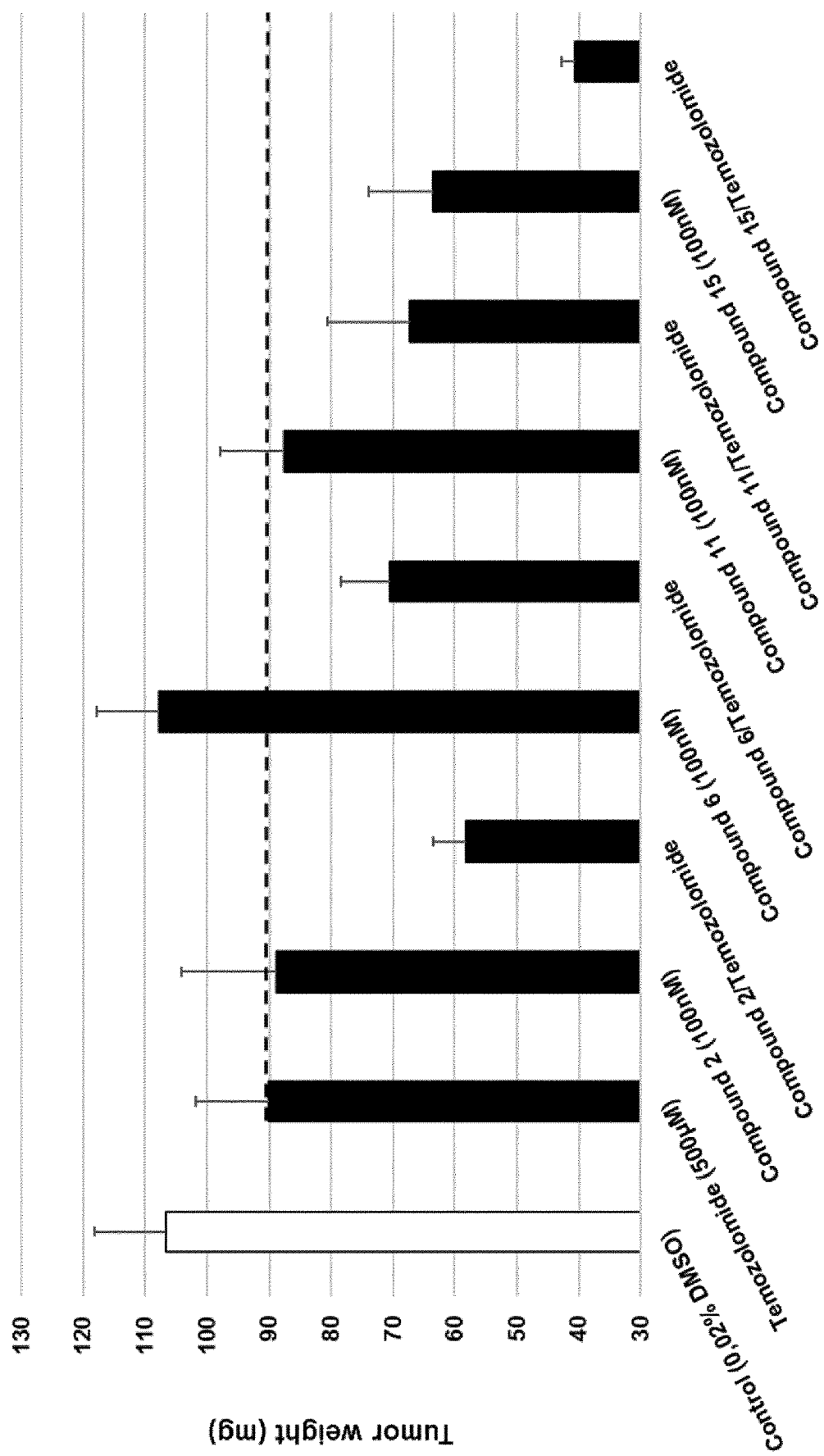
FIG. 2 shows the reduction of GL261 tumor weight upon treatment with temozolomide alone (500 microM) and the synergistic reduction of GL261 tumor weight upon treatment with the combination of compound 2 or 6 or 11 or 15 and temozolimide as compared to the control. The compounds 2, 11 and 15 alone (100 nM) reduces the tumor size and thus have anti-tumor activity. The compound 6 alone (100 nM) is having no effect on tumor size reduction. The combination of compound 2, 6, 11 or 15 and temozolomide is having synergistic effect to reduce the tumor size, as compared to temozolomide alone.

Compound 2 (2-(2-chlorobenzylidene)hydrazinecarboximidamide) alone (100 nM) reduces the tumor size. Together compound 2 (100 nM) and temozolimide (500 microM) have a synergistic effect to reduce the tumor size on the upper CAM compare to temozolomide alone or compound 2 alone (FIG. 2).

Compound 3 (2-(2-chlorobenzylidene)hydrazinecarboximidamide acetate) alone (100 nM) has no or a weak effect to reduce the tumor size. Together compound 3 (100 nM) and temozolomide (500 microM) have a synergistic effect to reduce the tumor size on the upper CAM compare to temozolomide alone or compound 3 alone (FIG. 1).

Compound 6 (2-[(3-chloropyridin-4-yl)methylidene]hydrazinecarboximidamide acetate) alone (100 nM) has no effect to reduce the tumor size. Together compound 6 (100 nM) and temozolomide (500 microM) have a synergistic effect to reduce the tumor size on the upper CAM compare to temozolomide alone or compound 6 alone (FIG. 2).

Compound 11 (2-(2-chlorobenzyl)-N'-(3-methylbutoxy) hydrazinecarboximidamide formate salt) alone (100 nM) reduces the tumor size. Together compound 11 (100 nM) and temozolomide (500 microM) have a synergistic effect to reduce the tumor size on the upper CAM compare to temozolomide alone or compound 11 alone (FIG. 2).

Compound 15 (2-(2-chlorobenzylidene)-N'-(prop-2-en-1-yloxy)hydrazine carboximidamide) alone (100 nM) reduces the tumor size. Together compound 15 (100 nM) and temozolimide (500 microM) have a synergistic effect to reduce the tumor size on the upper CAM compare to temozolomide alone or compound 15 alone (FIG. 2).

Together compound 22 (100 nM) and temozolimide (500 microM) have a synergistic effect to reduce the tumor size on the upper CAM compared to temozolomide (FIG. 1).

Figure 3:
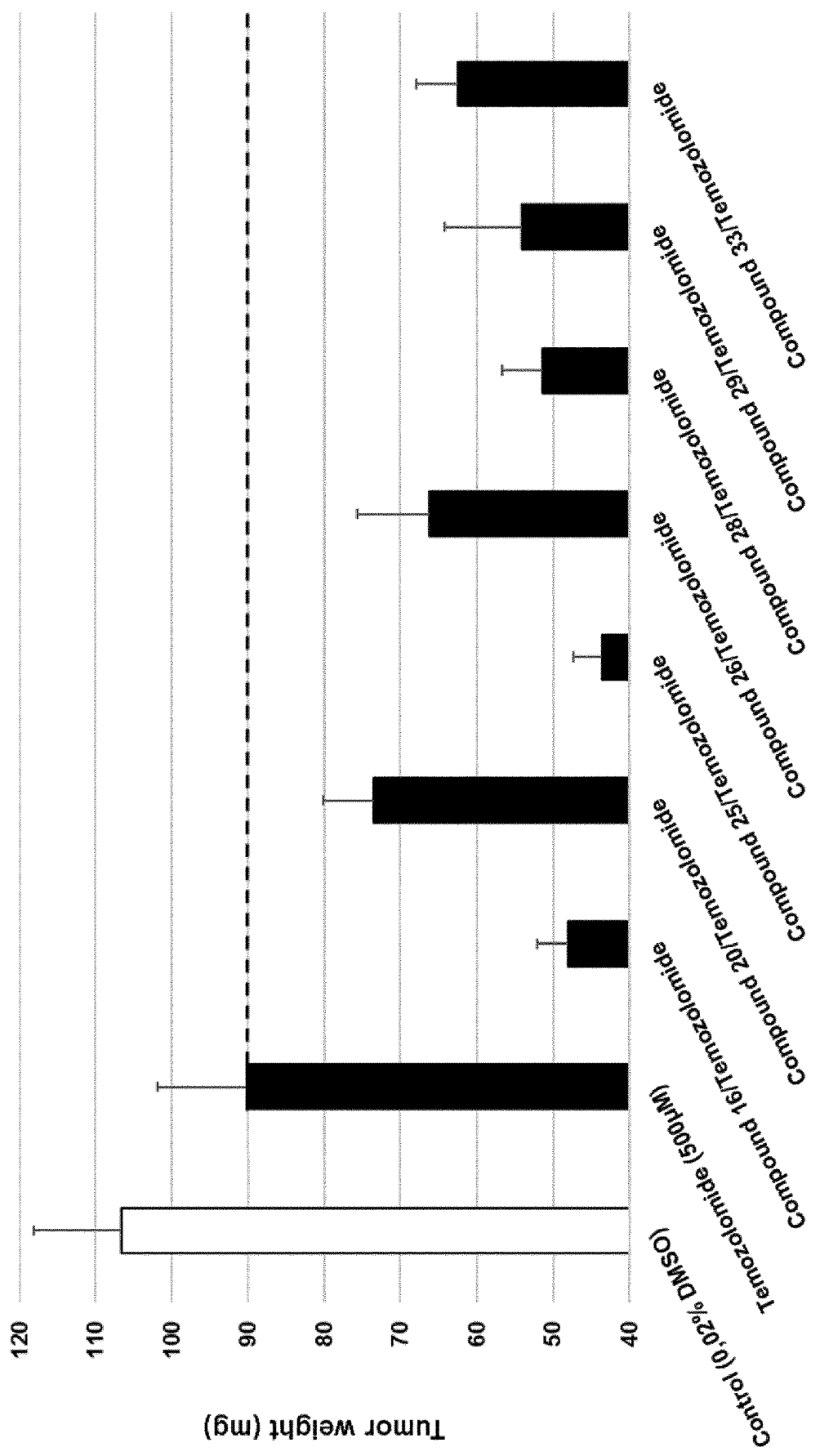
FIG. 3 shows the reduction of GL261 tumor weight upon treatment with temozolomide alone (500 microM) and the further reduction of GL261 tumor weight upon treatment with the combination of compound 16 or 20 or 25 or 26 or 28 or 29 or 33 and temozolimide as compared to the control. The negative control contains no Temozolomide but DMSO.

The compounds 16, 20, 25, 26, 28, 29 and 33 alone at 100 nM display anti-glioma activity by reducing the tumor size. Compounds 16, 20, 25, 26, 28, 29 or 33 associated with temozolimide (500 microM) further reduce the tumor size on the upper CAM compared to temozolomide alone or to compound 16, 20, 25, 26, 28, 29 or 33 alone respectively (FIG. 3).

No significant toxicity was observed with the test compounds and the survival of the chicken embryos were similar for all the treatments.

Results are summarized in the following table:

TABLE 1

Mean value (N = 18), SEM and p-value of tumor weight (mg) for each experimental group after 10 days of treatment

|  | Tumor weight (mg) (N = 18) | SEM | p (Temozolomide) |
|---|---|---|---|
| Control (0.02% DMSO) | 120.5 | 10.5 |  |
| Temozolomide (500microM) | 86.3 | 11.6 |  |
| Guanabenz (100 nM) | 115 | 32.1 |  |
| Guanabenz/Temozolomide (100 nM/500microM) | 68.3 | 15.5 | 2.76E−03 |
| Compound 3 (100 nM) | 111.0 | 27.6 | 2.85E−03 |
| Compound 3/Temozolomide (100 nM/500microM) | 65.1 | 9.9 | 1.23E−14 |
| Compound 22/Temozolomide (100 nM/500microM) | 48.4 | 12.1 | 5.15E−09 |

TABLE 2

Mean value (N = 7 to 12), SEM and p-value of tumor weight (mg) for each experimental group after 10 days of treatment

|  | Tumor weight (mg) (N = 7 to 12) | SEM | p(Temozolomide) < 0.05 |
|---|---|---|---|
| Control (0.02% DMSO) | 106.65 | 11.51 |  |
| Temozolomide (500 μM) | 90.17 | 11.67 |  |
| Compound 2 (100 nM) | 88.78 | 15.41 |  |
| Compound 2/Temozolomide (100 nM/500 μM) | 58.22 | 5.346 | * |
| Compound 6 (100 nM) | 107.76 | 9.96 |  |
| Compound 6/Temozolomide (100 nM/500 μM) | 70.45 | 8.015 |  |
| Compound 11 (100 nM) | 87.63 | 10.24 |  |
| Compound 11/Temozolomide (100 nM/500 μM) | 67.29 | 13.34 |  |
| Compound 15 (100 nM) | 63.44 | 10.46 |  |
| Compound 15/Temozolomide (100 nM/500 μM) | 40.66 | 2.14 | * |
| Compound 16/Temozolomide (100 nM/500 μM) | 48.11 | 3.969 | * |
| Compound 20/Temozolomide (100 nM/500 μM) | 73.51 | 6.68 |  |
| Compound 25/Temozolomide (100 nM/500 μM) | 43.6 | 3.68 | * |
| Compound 26/Temozolomide (100 nM/500 μM) | 66.23 | 9.52 |  |
| Compound 28/Temozolomide (100 nM/500 μM) | 51.33 | 5.428 | * |
| Compound 29/Temozolomide (100 nM/500 μM) | 54.13 | 10.01 | * |
| Compound 33/Temozolomide (100 nM/500 μM) | 62.42 | 5.49 |  |

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

What is claimed is:

1. A combination of:
   a first active agent selected from the group consisting of a compound of formula (I), and a pharmaceutically acceptable salt thereof,

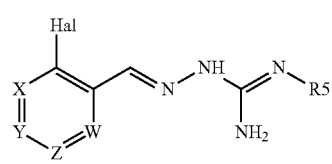

wherein:
   Hal=Cl or F,
   W is CR4;
   X is CR1;
   Y is either CR2 or N;
   Z is CR3;
   R1 is H or Hal;
   R2 is H or Hal;
   R3 is H or Hal;
   R4 is selected from is the group consisting of H, Cl and F;
   R5 is O—R7 or H;
   R7 is alkyl or alkenyl, optionally substituted with one or more R8 groups;
   R8 is H;
   or a prodrug, tautomer, or a pharmaceutically acceptable salt thereof,
   wherein said first active agent is not guanabenz,
   wherein said first active agent is in oral, intravenous, epidural, intracerebral or intracerebroventricular route dosage form; and
   a second active agent, which is temozolomide, a prodrug thereof, or a pharmaceutically acceptable salt thereof,
   where the first and second active agents are configured for simultaneous or sequential use.

2. The combination according to claim 1, wherein the first active agent is in an oral dosage form.

3. The combination according to claim 1, wherein the second active agent is in an oral or intravenous dosage form.

4. The combination according to claim 1, wherein the first and second active agents are in oral dosage forms.

5. The combination according to claim 1, wherein the first and second active agents are in the same oral dosage form.

6. The combination according to claim 1, wherein in formula (I), R5=H, O—(C3-C6)alkyl, O(C2-C6)alkyl-OH, or O—(C1-C3)alkyl-S—(C1-C3)alkyl.

7. The combination according to claim 1, wherein the first active agent is 2 (2 chlorobenzylidene)-N-propoxyhydrazinecarboximidamide, a prodrug thereof, or a pharmaceutically acceptable salt thereof.

8. The combination according to claim 1, wherein the first active agent is selected from the group consisting of 2-(2-chlorobenzylidene)hydrazinecarboximidamide, 2-(2-chlorobenzylidene)hydrazine carboximidamide acetate, 2-(2-chlorobenzylidene)-N'-ethoxyhydrazinecarboximidamide, N'-butoxy-2-(2-chlorobenzylidene)hydrazinecarboximidamide, 2-[(3-chloropyridin-4-yl)methylidene]hydrazinecarboximidamide acetate, 2-(2-chlorobenzyl)-N'-(3-methylbutoxy)hydrazinecarboximidamide formate salt and 2-(2-chlorobenzylidene)-N'-(prop-2-en-1-yloxy) hydrazine carboximidamide, or a prodrug thereof or a pharmaceutically acceptable salt or the free form thereof.

9. A method of treating a glioma or for ameliorating effects of a glioma in a patient in need thereof, said method comprising administering to the patient a combination as defined in claim 1.

10. The method according to claim 9 where said first active agent is in an oral dosage form and said second active agent is in an oral or an intravenous dosage form.

11. The method according to claim 9, wherein the glioma is a multiform glioblastoma.

12. A pharmaceutical composition comprising the combination according to claim 1 and a pharmaceutically acceptable carrier.

13. The pharmaceutical composition according to claim 12 where said first active agent is in an oral dosage form and said second active agent is in an oral or an intravenous dosage form.

* * * * *